(12) United States Patent
Nathan et al.

(10) Patent No.: US 11,090,275 B2
(45) Date of Patent: Aug. 17, 2021

(54) COMPOSITIONS COMPRISING CANNABIDIOL AND SECOND THERAPEUTIC AGENTS FOR THE TREATMENT OF CANCER

(71) Applicant: JAY PHARMA, INC., Toronto (CA)

(72) Inventors: Ilana Nathan, Tel Aviv (IL); Zvi Vogel, Rehovot (IL); Lakshmi Narasaiah Uppalapati, Kadapa (IN); Adela Juknat Geralnik, Rehovot (IL)

(73) Assignee: JAY PHARMA INC., Toronto (CA)

( * ) Notice: Subject to any disclaimer, the term of this patent is extended or adjusted under 35 U.S.C. 154(b) by 0 days.

(21) Appl. No.: 15/771,816

(22) PCT Filed: Oct. 27, 2016

(86) PCT No.: PCT/IL2016/051166
§ 371 (c)(1),
(2) Date: Apr. 27, 2018

(87) PCT Pub. No.: WO2017/072773
PCT Pub. Date: May 4, 2017

(65) Prior Publication Data
US 2018/0311182 A1 Nov. 1, 2018

Related U.S. Application Data

(60) Provisional application No. 62/246,780, filed on Oct. 27, 2015.

(51) Int. Cl.
| | | |
|---|---|---|
| A61K 31/05 | (2006.01) | |
| A61K 31/137 | (2006.01) | |
| A61K 31/138 | (2006.01) | |
| A61K 31/201 | (2006.01) | |
| A61K 31/202 | (2006.01) | |
| A61K 31/40 | (2006.01) | |
| A61P 35/00 | (2006.01) | |
| A61K 31/122 | (2006.01) | |
| A61K 31/575 | (2006.01) | |
| A61K 31/66 | (2006.01) | |
| A61K 45/06 | (2006.01) | |

(52) U.S. Cl.
CPC ............ *A61K 31/05* (2013.01); *A61K 31/122* (2013.01); *A61K 31/137* (2013.01); *A61K 31/138* (2013.01); *A61K 31/201* (2013.01); *A61K 31/202* (2013.01); *A61K 31/40* (2013.01); *A61K 31/575* (2013.01); *A61K 31/66* (2013.01); *A61K 45/06* (2013.01); *A61P 35/00* (2018.01)

(58) Field of Classification Search
CPC .... A61K 31/138; A61K 31/05; A61K 31/122; A61K 31/137; A61K 31/201; A61K 31/202; A61K 31/40; A61K 31/575; A61K 31/66; A61K 45/06; A61P 35/00
See application file for complete search history.

(56) References Cited

FOREIGN PATENT DOCUMENTS

| | | | | |
|---|---|---|---|---|
| GB | 2460672 | | 12/2009 | |
| GB | 2515312 | | 12/2014 | |
| WO | WO-9211035 A1 | * | 7/1992 | ............ A61K 31/135 |
| WO | WO-0149284 A1 | * | 7/2001 | ............ A61K 31/33 |
| WO | WO-2007001891 A1 | * | 1/2007 | ............ A61K 9/0014 |
| WO | WO-2008144475 A1 | * | 11/2008 | ............ A61K 31/35 |
| WO | 2009/147439 | | 12/2009 | |
| WO | WO-2015198071 A1 | * | 12/2015 | |

OTHER PUBLICATIONS

Rodriguez, "Know the Most Common Types of Cancer", Everyday Health, publ. online Feb. 8, 2010, pp. 1-13 (Year: 2010).*
Wistuba et. al., Nature Rev., Clin. Oncology, (2011), vol. 8, pp. 135-141 (Year: 2011).*
Bhatia et. al., Nature Biotechnology, (2012), vol. 30(7), pp. 604-610 (Year: 2012).*
Kaiser, Science, (2012), vol. 337, pp. 282-284 (Year: 2012).*
WIPO, International Search Report for International Application No. PCT/IL2016/051166, dated Mar. 28, 2017 (5 pages).

\* cited by examiner

*Primary Examiner* — Sarah Pihonak
(74) *Attorney, Agent, or Firm* — Haynes and Boone, LLP

(57) ABSTRACT

The invention provides synergistic combinations of cannabidiol (CBD) and a second therapeutic agent, such as one or more ChEH/AEBS inhibitors, a naphthoquinone or a derivative thereof, or any combination thereof, effective for the treatment cancer. Compositions containing same and methods of use of same are described.

17 Claims, 18 Drawing Sheets

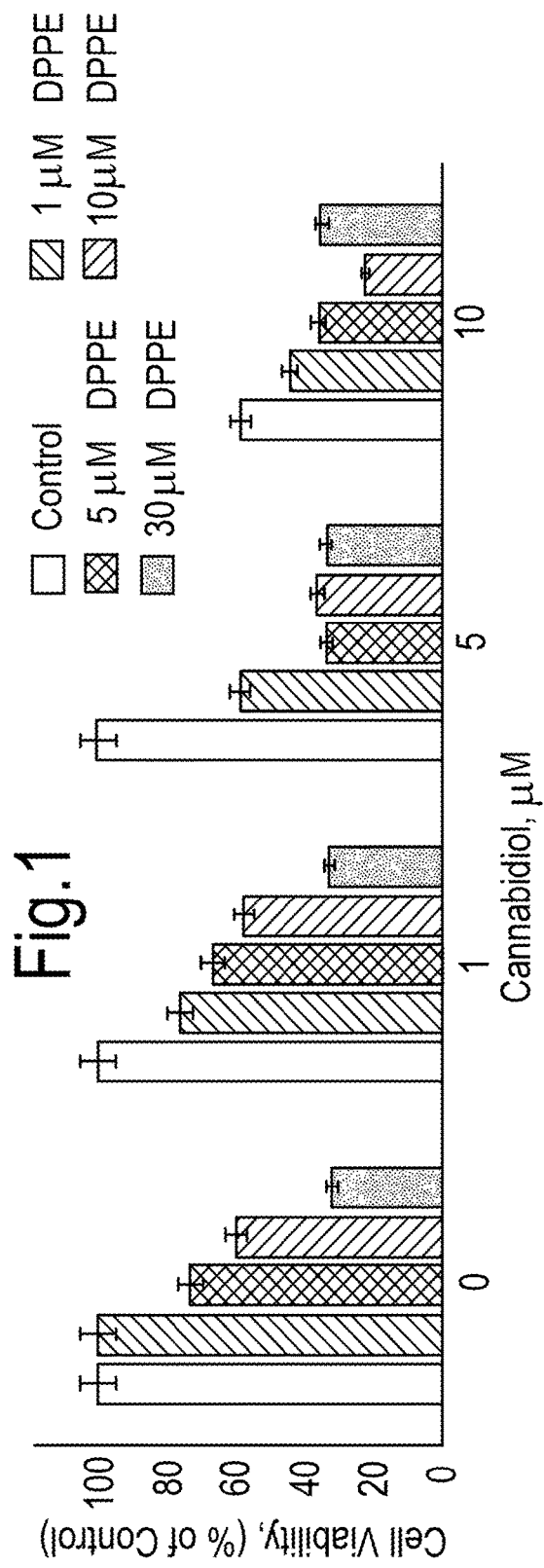
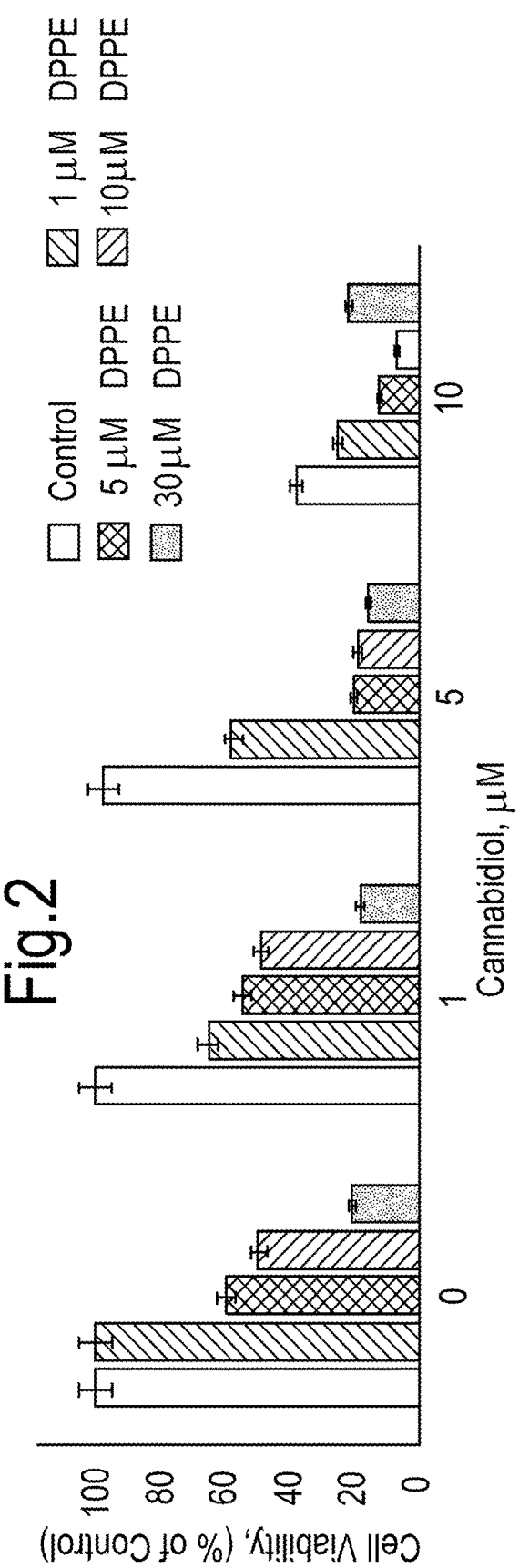

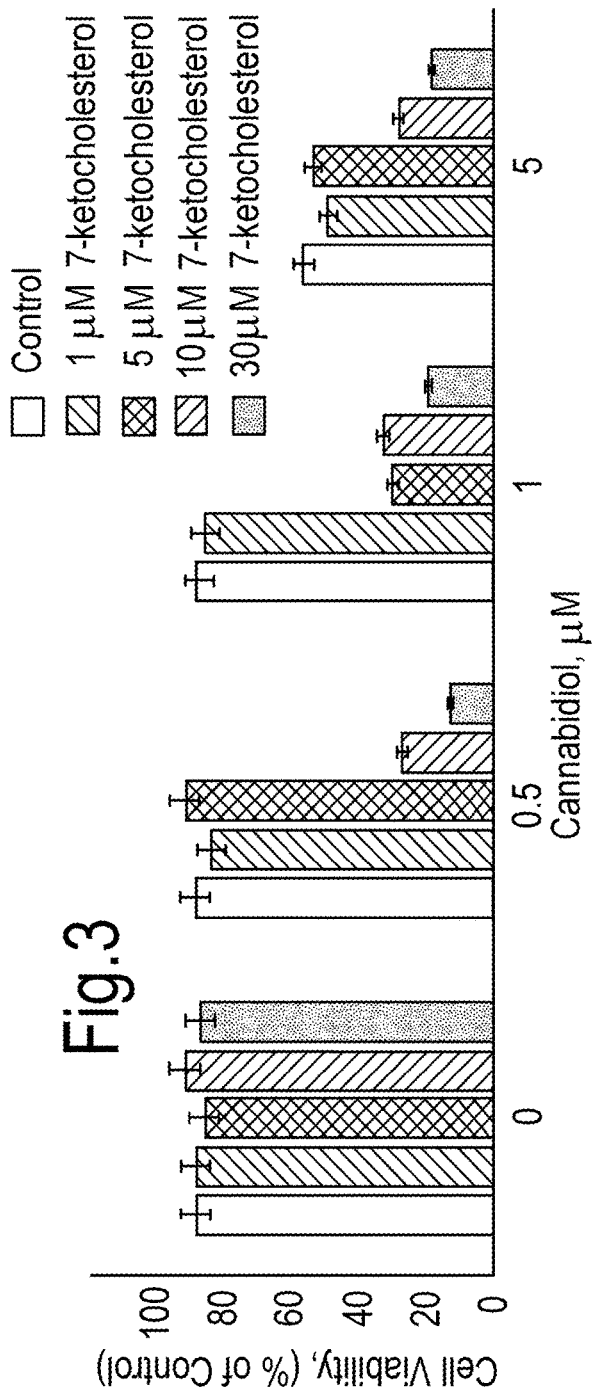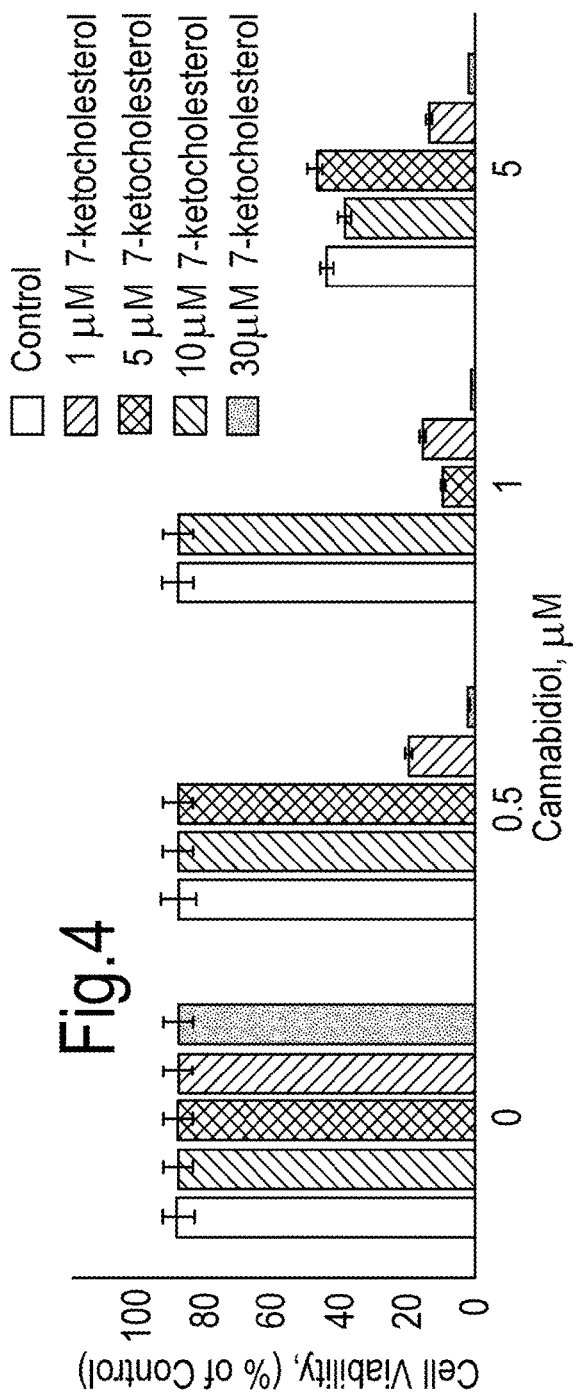

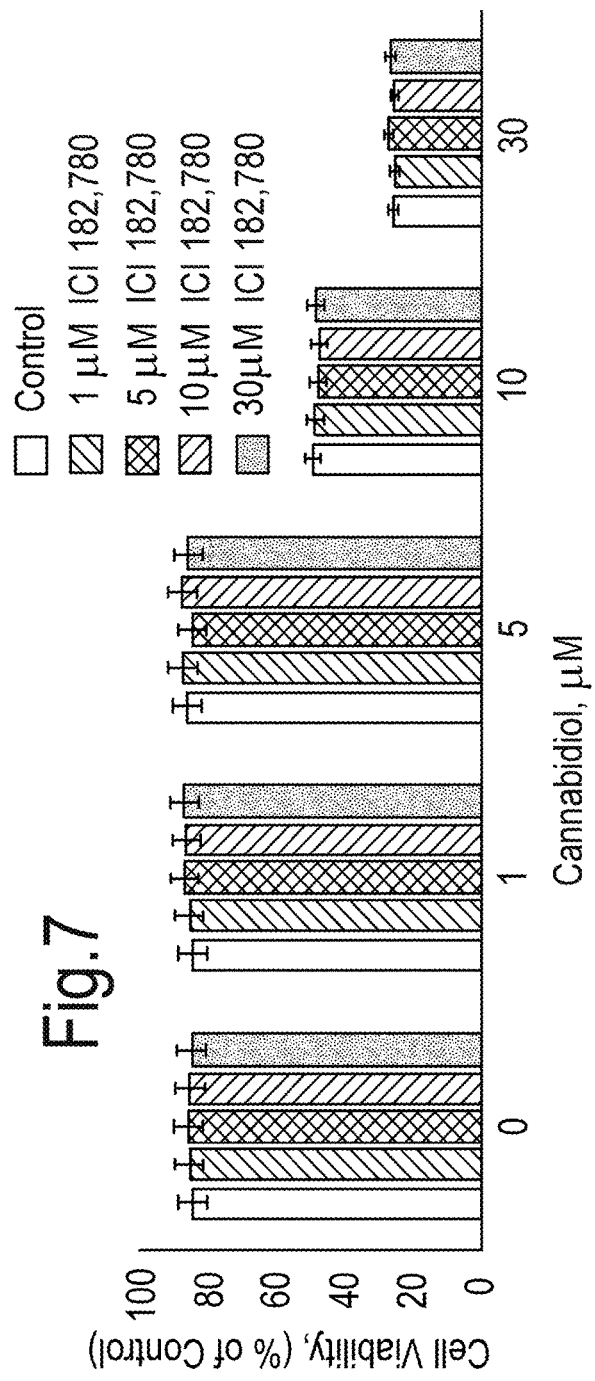
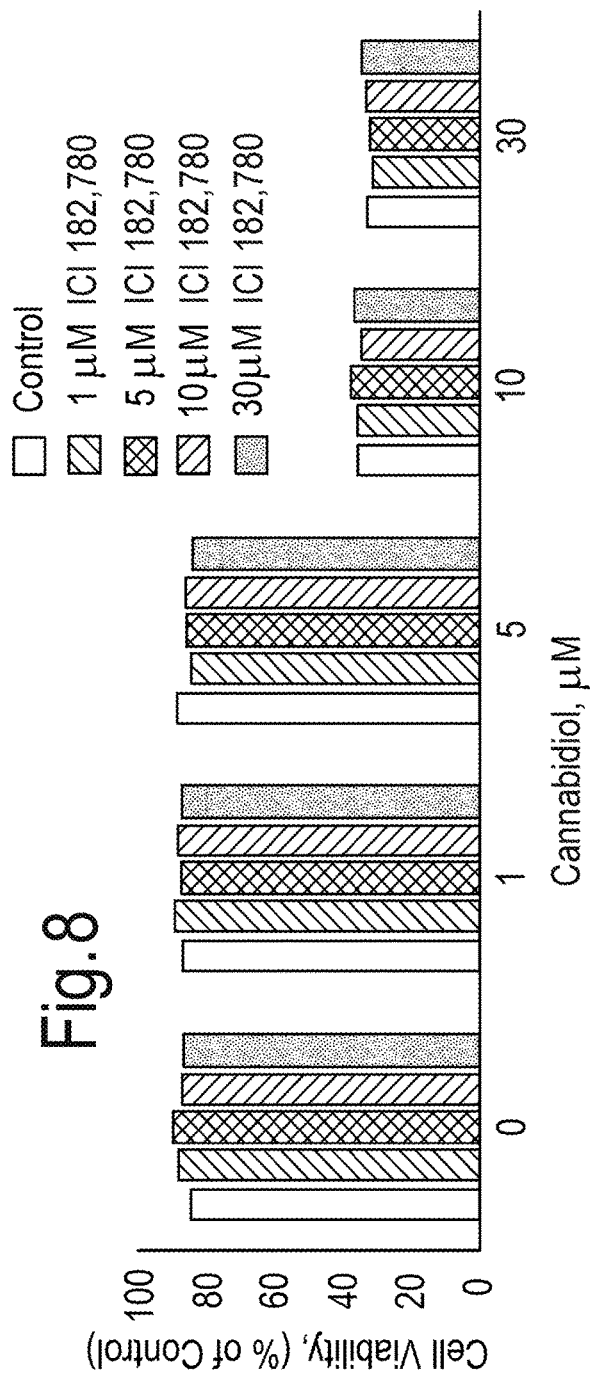

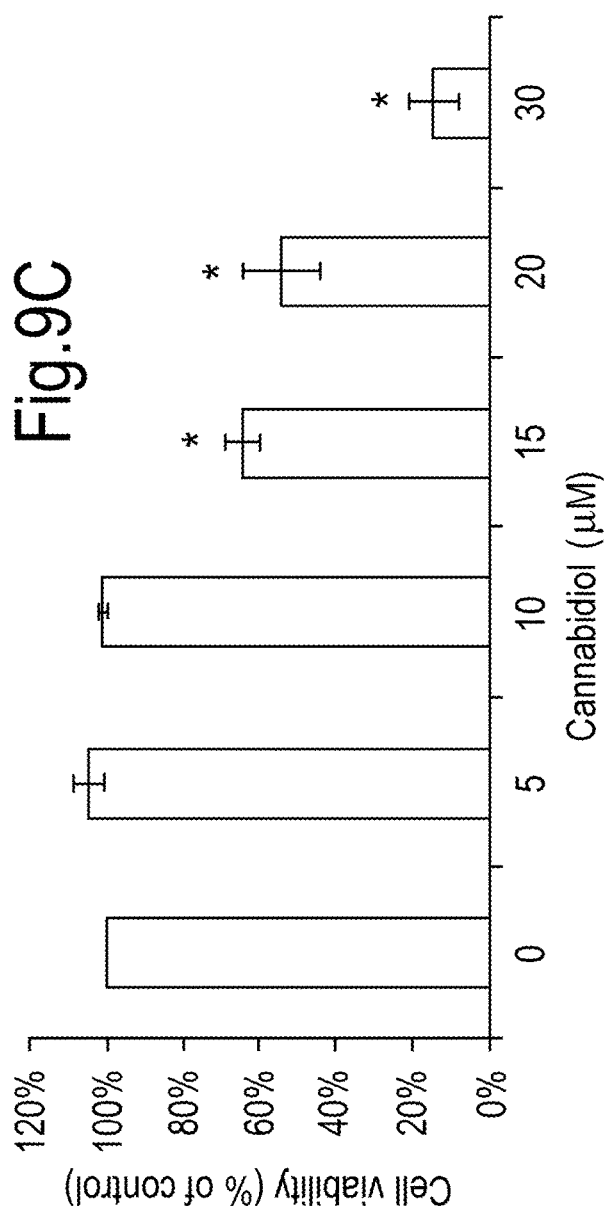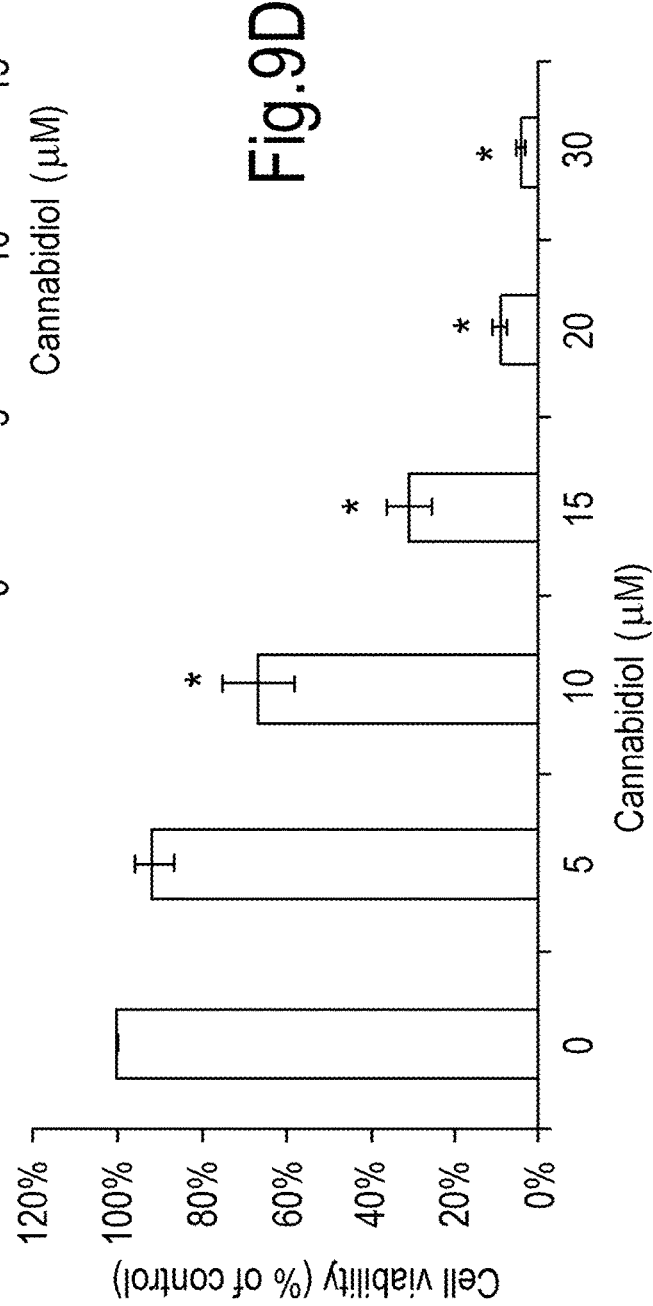

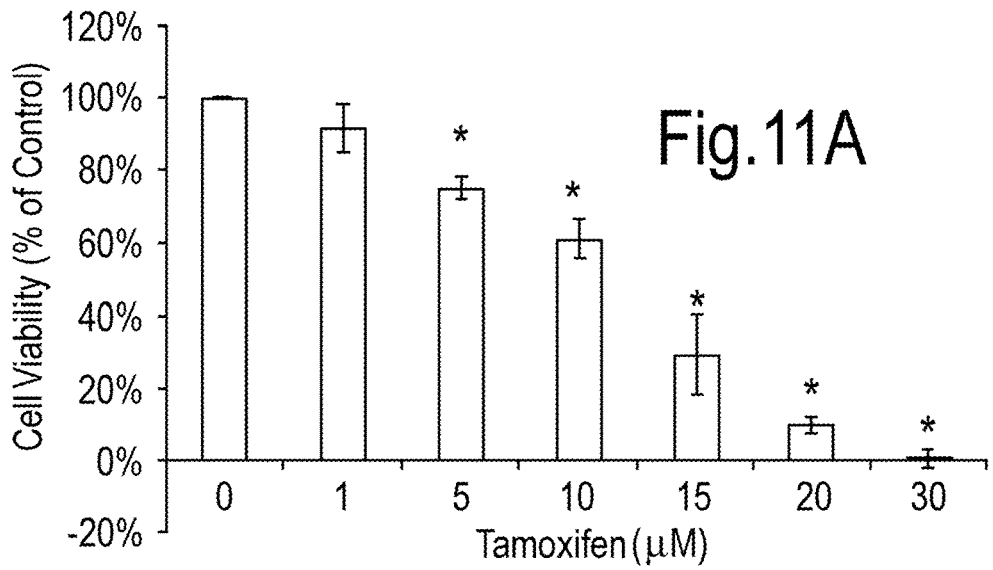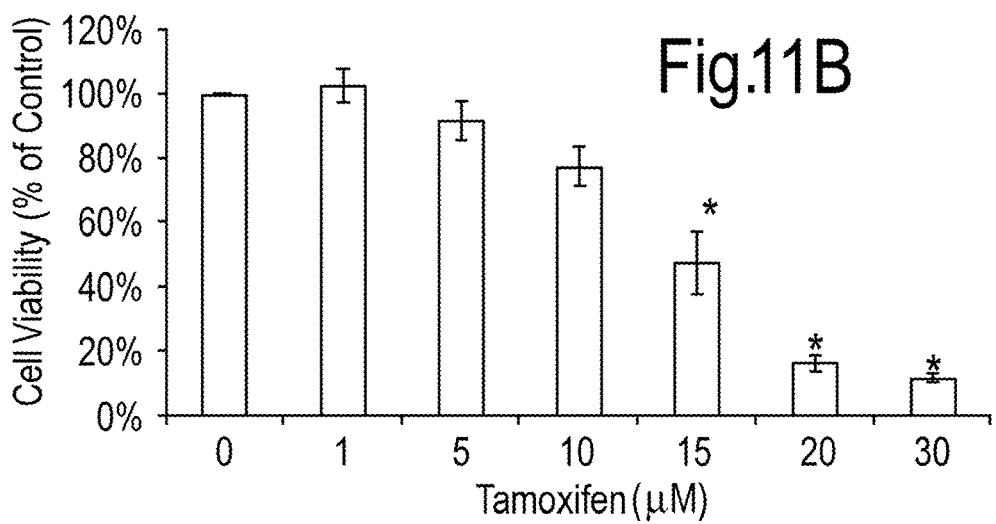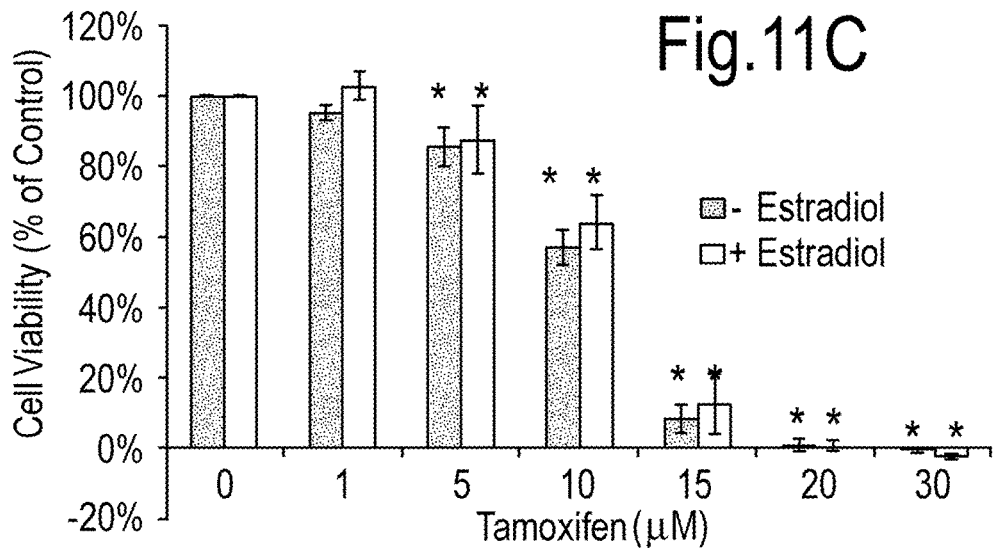

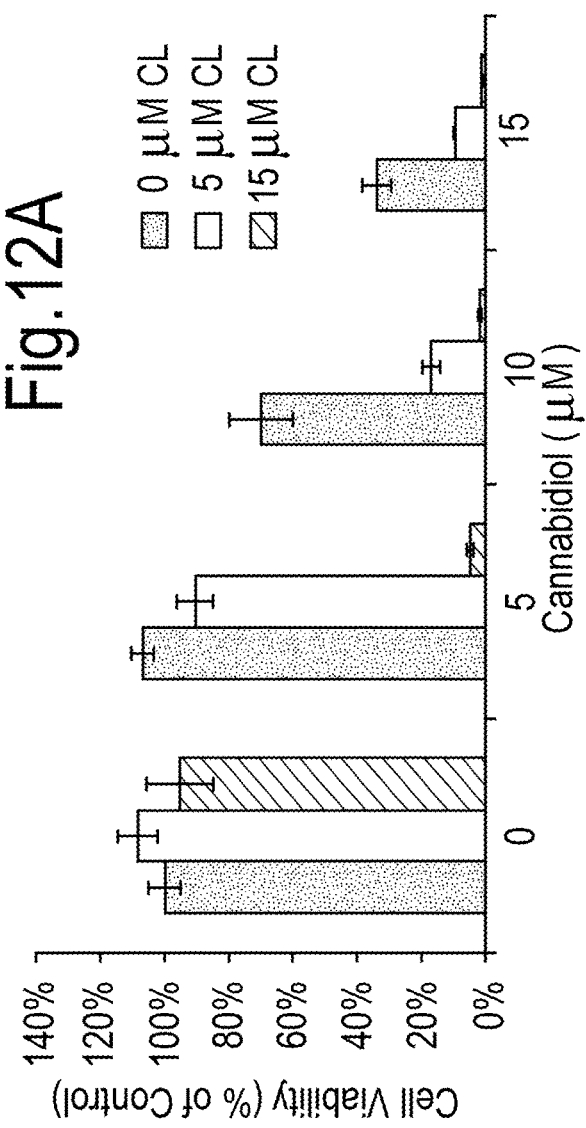
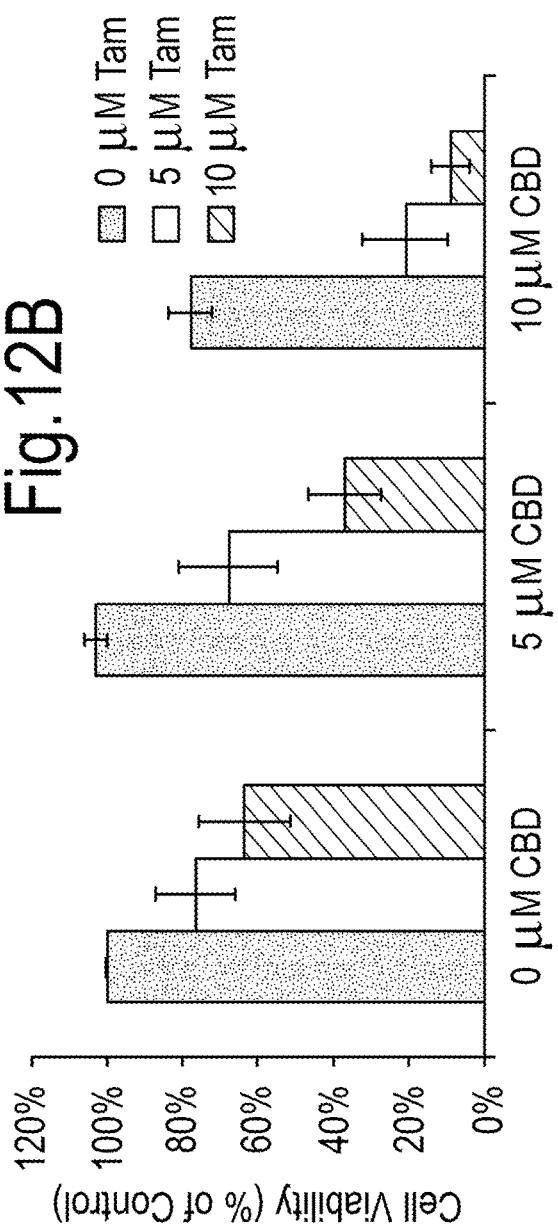

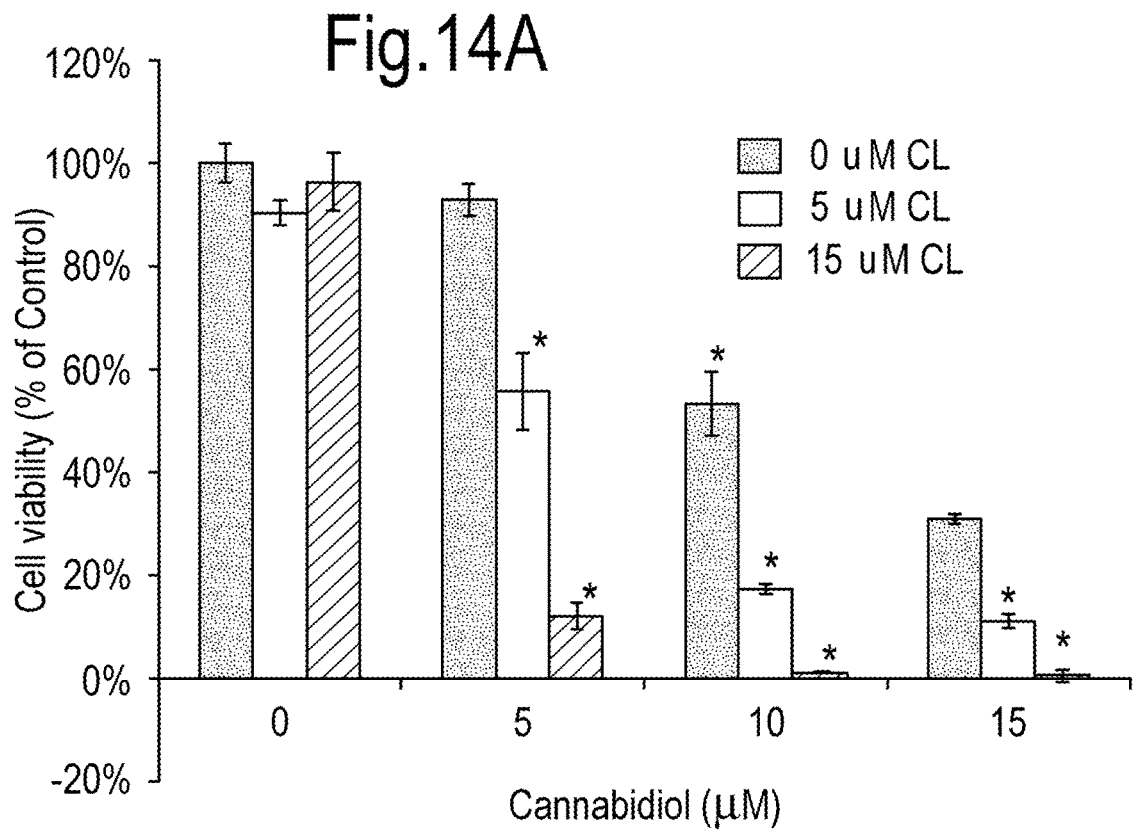
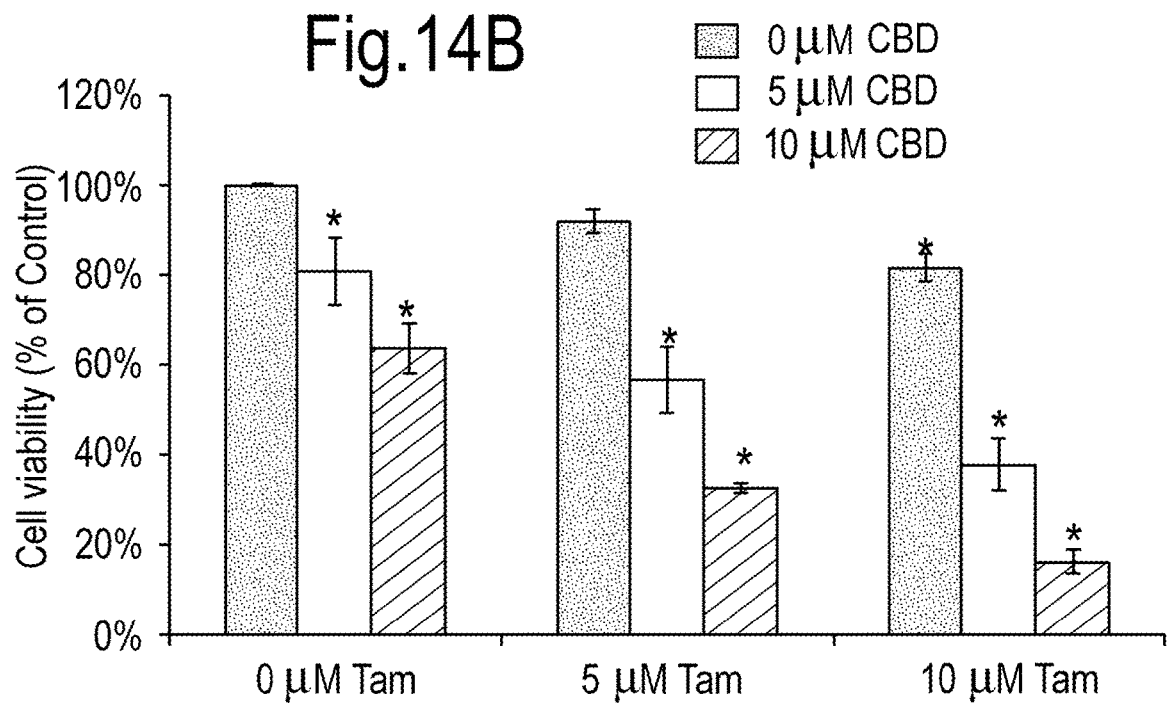

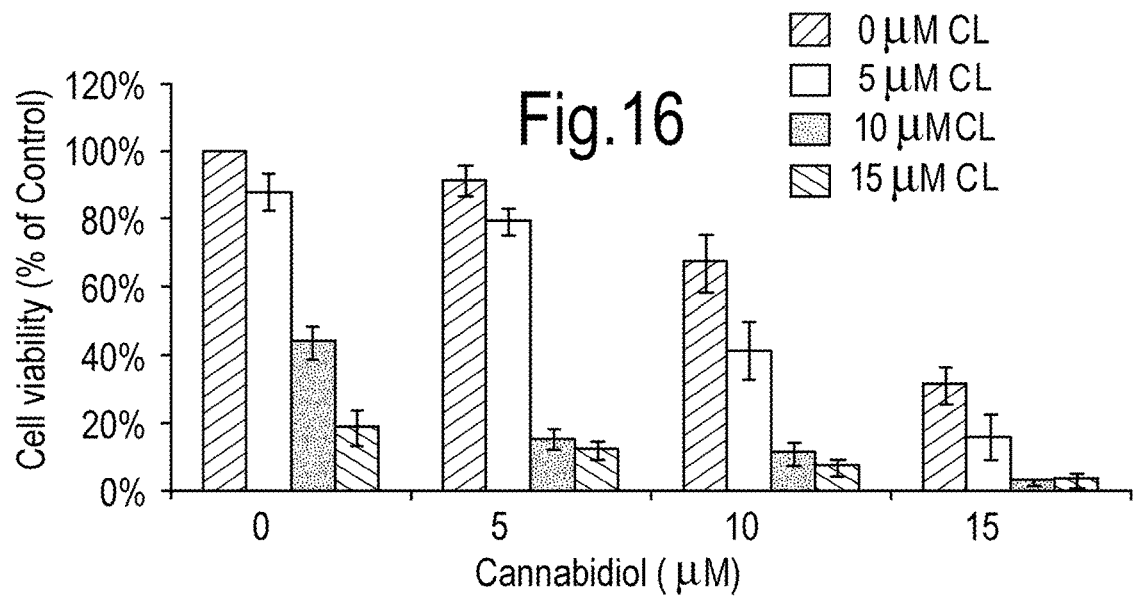
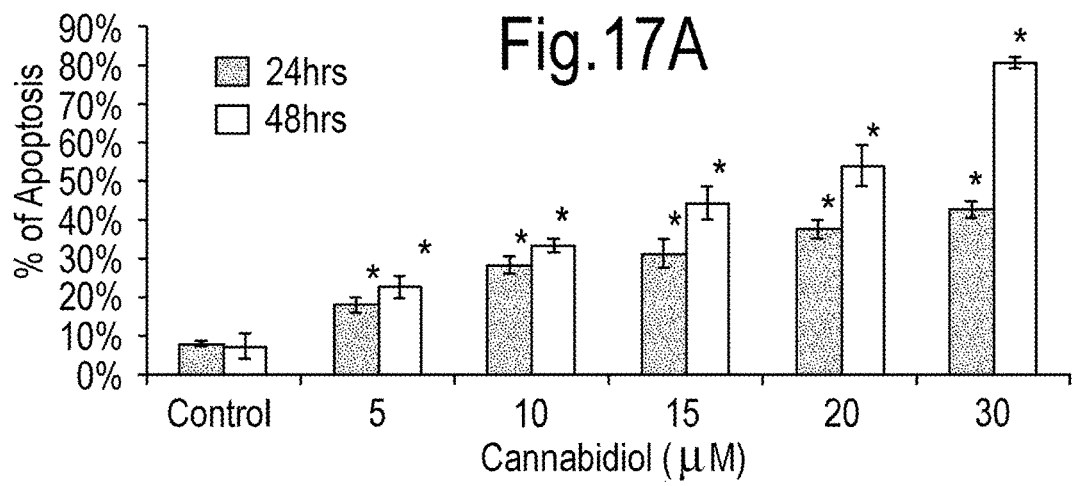
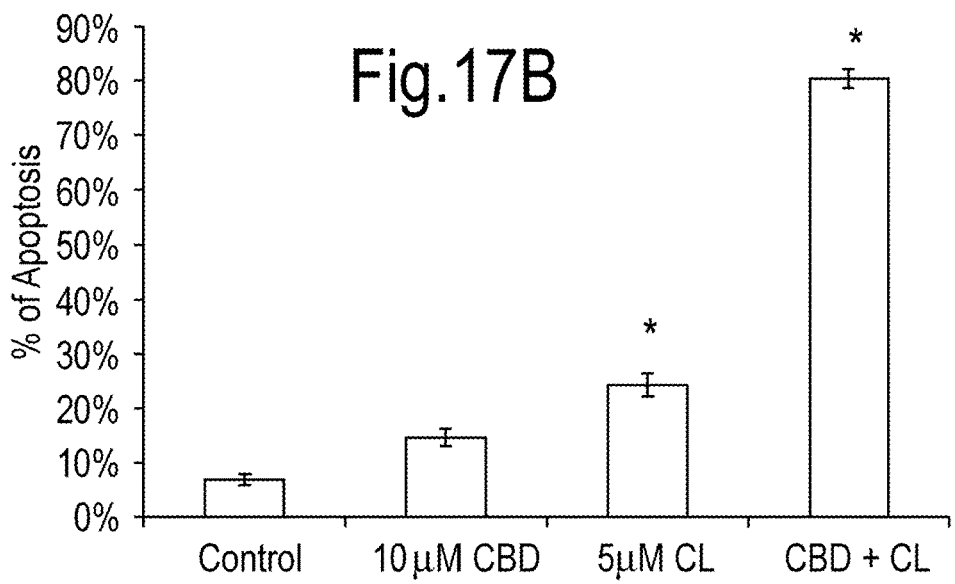

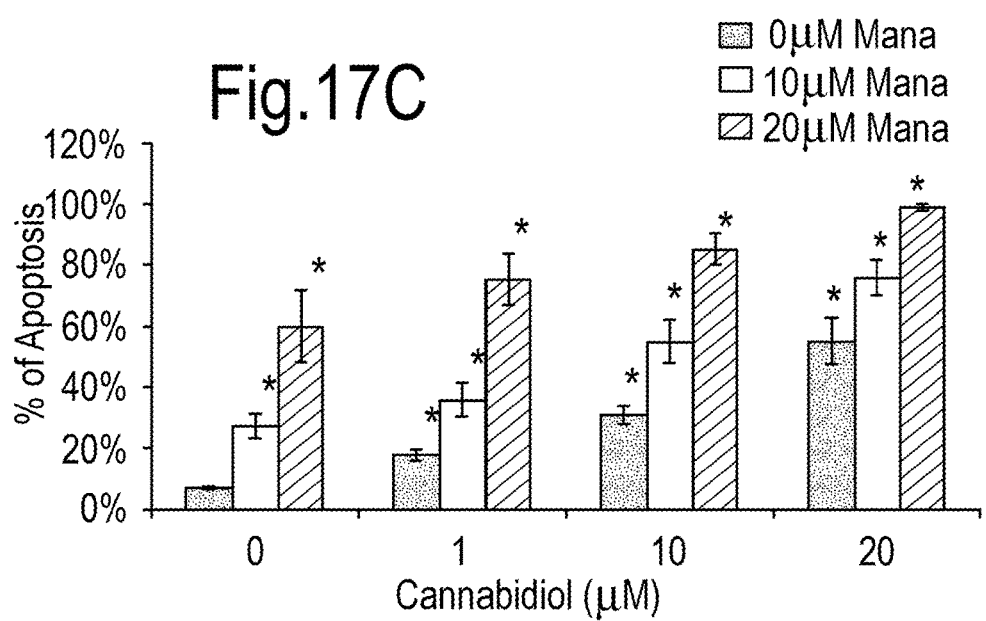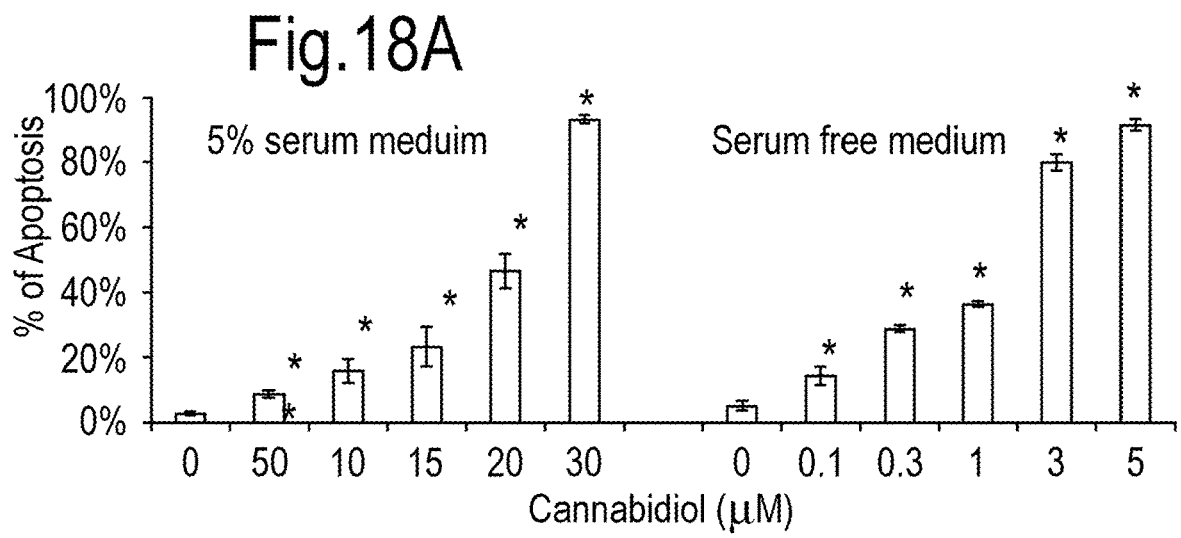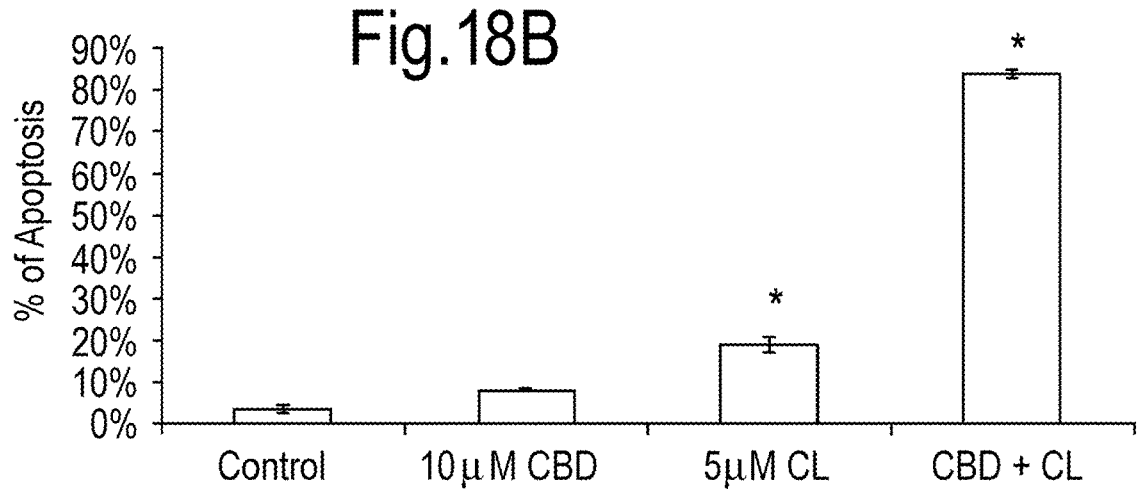

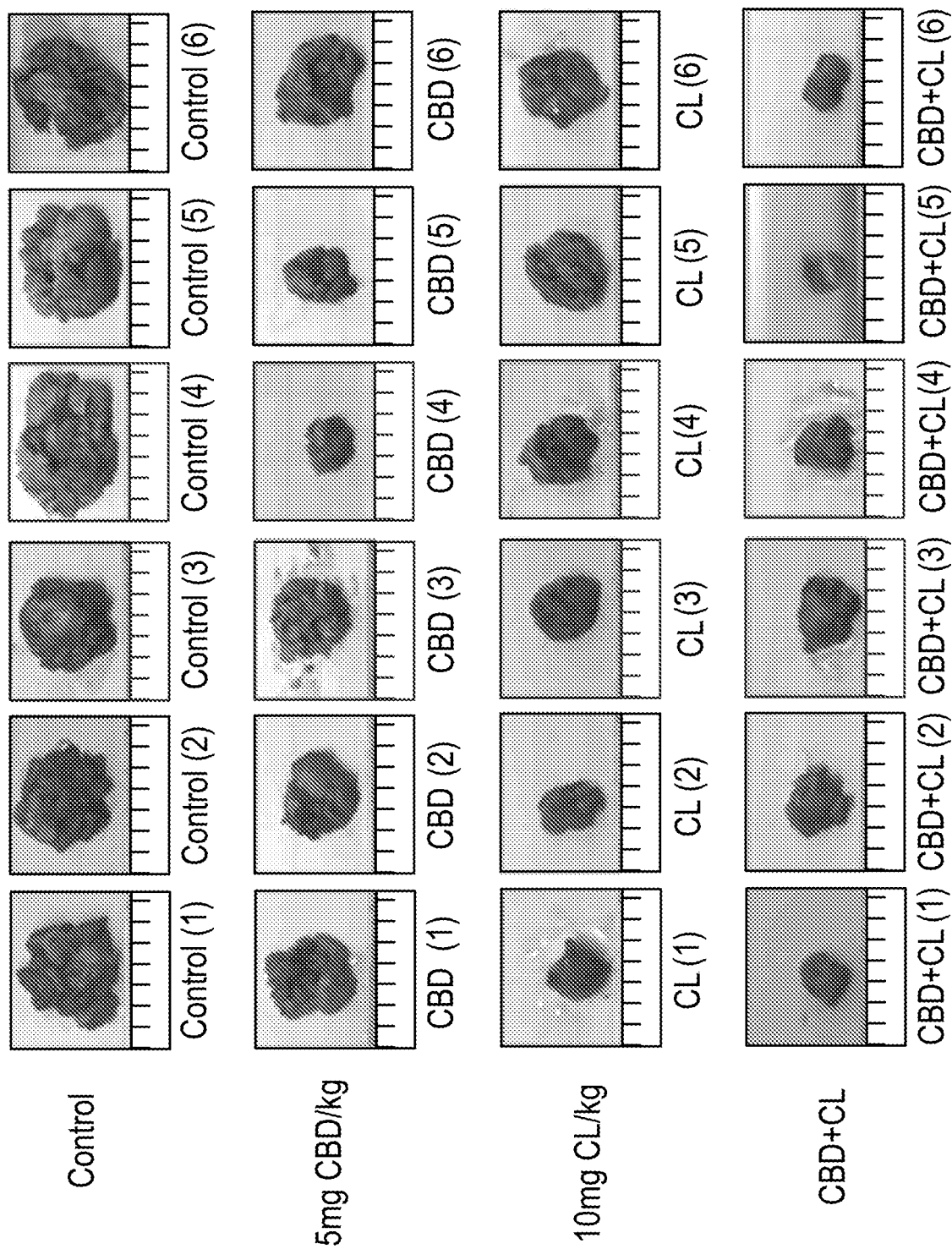

COMPOSITIONS COMPRISING CANNABIDIOL AND SECOND THERAPEUTIC AGENTS FOR THE TREATMENT OF CANCER

CROSS-REFERENCE TO RELATED APPLICATION(S)

This application is a § 371 national phase of International Application No. PCT/IL2016/051166, filed on Oct. 27, 2016, which claims the benefit of U.S. Provisional Application No. 62/246,780, filed on Oct. 27, 2015, the contents of each of which are hereby incorporated herein in their entirety by express reference thereto.

FIELD OF INVENTION

This invention is directed to combinations of cannabidiol and a second therapeutic agent effective in the treatment of cancer. The second therapeutic agent includes one or more ChEH/AEBS inhibitors, a naphthoquinone or a derivative thereof, or combinations thereof.

BACKGROUND OF THE INVENTION

Cannabidiol (CBD), a major non-psychoactive constituent of *cannabis*, is considered an anti-neoplastic agent on the basis of its in-vitro and in-vivo activity against tumor cells. Due to the lack of psychotropic activity, its pharmacology and therapeutic potential has been under intensive investigation. Recent studies have demonstrated that CBD possesses a variety of intriguing pharmacological activities, including immunosuppressive, anti-inflammatory, anti-convulsive, anxiolytic, anti-psychotic, neuro protective and anti-nausea effects. Its therapeutic potential has been further substantiated by the recent approval in Canada of a cannabinoid based medicine containing approximately equal amounts of $\Delta 9$-tetrahydrocannabinol (THC) and CBD, for alleviating neuropathic pain associated with multiple sclerosis.

Cancers are known to affect many areas of the body with the most common types of cancers including: cancer of the bile duct, cancer of the bladder, cancer of the bone, cancer of the bowel (including cancer of the colon and cancer of the rectum), cancer of the brain, cancer of the breast, cancer of the neuroendocrine system (commonly known as a carcinoid), cancer of the cervix, cancer of the eye, cancer of the esophagus, cancer of the head and neck (this group includes carcinomas that start in the cells that form the lining of the mouth, nose, throat, ear or the surface layer covering the tongue), Kaposi's sarcoma, cancer of the kidney, cancer of the larynx, leukemia, cancer of the liver, cancer of the lung, cancer of the lymph nodes, Hodgkin's lymphoma, non-Hodgkin's lymphoma, melanoma, mesothelioma, myeloma, cancer of the ovary, cancer of the pancreas, cancer of the penis, cancer of the prostate, skin cancer, soft tissue sarcomas, cancer of the spinal cord, cancer of the stomach, testicular cancer, cancer of the thyroid, cancer of the vagina, cancer of the vulva and cancer of the uterus.

Conventional cancer treatment options are often limited by toxicity or acquired resistance, and novel agents are needed. Cannabidiol (CBD), is a potent, natural compound with reported activity on many cancer types. CBD belongs to the cannabinoid family, a group of pharmacologically active compounds that bind to specific G-proteincoupled receptors. Phytocannabinoids are plant-derived products from *Cannabis sativa*; endogenous cannabinoids are made in animal and human tissues; and synthetic cannabinoids are laboratory produced. The G proteincoupled receptor CB1 is found mainly in the brain and nervous system, whereas CB2 is expressed predominantly by immune cells. Recent data suggest that some cannabinoids also elicit signal through the vanilloid receptor, whereas others may function in a receptor independent manner Cannabinoids can modulate signaling pathways central to the growth and spread of cancer. They inhibit cell-cycle progression and chemotaxis, and block angiogenesis. Recent studies have shown that cannabinoids also induce autophagic cell death. $\Delta 9$-tetrahydrocannabinol (THC) is one of the best-characterized cannabinoids; however, its therapeutic applications are limited by its psychoactive effects.

There have been some reports of the utility of CBD combination therapy with selective estrogen receptor modulators (SERMs), but there is only limited information as to the true utility of this treatment regimen.

There remains a need for new cancer therapies that are more effective and are effective against other cancer types than the available agents and therapies to date.

In one embodiment, the present invention provides a composition comprising cannabidiol (CBD) and a second therapeutic agent, effective for the treatment of cancer. In one aspect, the second therapeutic agent is a naphthoquinone or a derivative thereof. In another aspect, the second therapeutic agent is a ChEH/AEBS inhibitor compound. In some embodiments, the second therapeutic agent is one or more of a naphthoquinone and/or derivative a thereof, one or more ChEH/AEBS inhibitor compounds, or any combination thereof. The compositions are envisioned for use in the treatment of cancer, and in some embodiments, treatment of estrogen receptor negative cancers are envisioned and in some embodiments, estrogen receptor positive cancers are envisioned.

In one embodiment this invention provides compositions comprising combinations of cannabidiol and at least one second therapeutic agent, which is part of the class of ChEH/AEBS inhibitors and uses of same in the treatment of cancer.

ChEH/AEBS inhibitors comprise different pharmacological classes of natural or synthetic compounds. Cholesterol epoxide hydrolase (ChEH) catalyzes the hydration of cholesterol-5,6-epoxides (5,6-EC) into cholestane-$3\beta,5\alpha,6\beta$-triol. ChEH is a hetero-oligomeric complex called the microsomal anti-estrogen binding site (AEBS) comprising 3bhydroxysterol-D8-D7-isomerase (D8D7I) and 3b-hydroxysterol-D7-reductase (DHCR7). D8D7I and DHCR7 regulate cholesterol biosynthesis and tumor cells growth differentiation, death and cancer progression.

ChEH/AEBS inhibitors comprise a number of compounds, including, inter alia, tesmilifene (DPPE, N,N0-diethylamino-4-(phenylmethylphenoxy)-ethanamine,HCl)3 PBPE, PCPE, MBPE, MCPE, PCOPE, MCOPE, MCOCH2PE; sigma receptor ligands such as SR31747A, BD10008, Haloperidol, SR-31747A, Ibogaine, AC-915, Rimcazole, Trifluoroperazine, Amiodarone; cholesterol biosynthesis inhibitors such as Triparanol, Terbinafine, U-18666A, Ro 48-8071, AY9944, SKF-525A; unsaturated fatty acids such as oleic acid, $\alpha$-linolenic acid, acidarachidonic acid (ARA), docosahexaenoic acid (DHA); ring B oxysterols such as 6-Ketocholestanol, 7-Ketocholestanol, 7-Ketocholesterol, $7\alpha$-hydroxycholesterol, $7\beta$-Hydroxycholesterol, 6-Keto-5 hydroxycholestanol Cholestane-$3\beta,5\alpha,6\beta$-triol(CT) and others as will be appreciated by the skilled artisan (see for example, Silvente-Poirot S, Poirot M. Cholesterol epoxide hydrolase and cancer. Current opinion in pharmacology. 2012; 12(6):696-703; de Medina P, Paillasse M R, Segala G, Poirot M, Silvente-Poirot S:Identification and pharmacological characterization of cholesterol-5,6-epoxide hydrolase as a target for tamoxifen and AEBS ligands. Proc Natl Acad Sci USA 2010, 107:13520-13525, all of which are hereby incorporated in their entirety by reference herein).

In another embodiment, the second therapeutic agent is naphthoquinone or a derivative thereof.

The combination therapy/compositions of this invention are active via an estrogen receptor independent mechanism and in some embodiments, the invention specifically contemplates compositions for use in treating estrogen receptor negative cancers/tumors.

According to this aspect, and in some embodiments, the ChEH/AEBS inhibitors for use in the described combination therapy may include selective estrogen receptor modulators (SERMs), which contain a cationic aminoethoxy side chain, such as clomiphene, tamoxifen, 4-hydroxy-tamoxifen, raloxifene, Nitromiphene, Ru 39,411 but specifically excludes non-cationic antiestrogens, such as Faslodex, ICI-164,384 and RU-58.

The compositions of this invention were shown in the Examples, as presented herein to possess anticancer activity, when multiple classes of ChEH/AEBS inhibitors were used (Example 1).

The compositions of this invention were shown in the Examples, as presented herein to possess anticancer activity as well, for example, antileukemic activity, and same is clearly mediated via an estrogen receptor-independent mechanism, as combination treatment with clomiphene and CBD inhibited the CCRF-CEM line, which does not contain an estrogen receptor.

According to this aspect, with reference to estrogen receptor free cancers/tumors, in one embodiment, the ChEH/AEBS inhibitor is a triphenylethylene (TPE) or a derivative thereof. In another embodiment, the triphenylethylene derivative is selected from the group comprising: antiestrogens (AEs), clomiphene (CL), and tamoxifen (Tam), or a combination thereof.

This invention provides a composition comprising a synergistic combination of cannabidiol (CBD) and at least one ChEH/AEBS inhibitor compound, which ChEH/AEBS inhibitor compound is not a SERM. In some embodiments, the ChEH/AEBS inhibitor compound is a selective inhibitor of ChEH/AEBS, and in some embodiments, the selective inhibitor of ChEH/AEBS is PBPE or tesmilifene (DPPE).

In some embodiments, the inhibitor is a cholesterol biosynthesis inhibitor, which in some emboidments, is Triparanol, Teribinafine or U-18666A, or combinations thereof.

In some embodiments, the inhibitor compound is a ring B oxysterol, which in some embodiments, is 6-ketocholestanol, 7-ketocholestanol, 7-ketocholesterol and Cholestane-3b,5a,6b-triol(CT) or combinations thereof.

In some embodiments, the inhibitor compound is an unsaturated fatty acid, which in some embodiments, is oleic acid, arachidonic acid (ARA) or docosahexaenoic acid (DHA) or combinations thereof.

In some embodiments, the inhibitor compound is naphthoquinone or a derivative thereof. In some embodiments, the compound is menadione or a derivative thereof.

This invention provides a composition comprising a synergistic combination of cannabidiol (CBD) and at least one ChEH/AEBS inhibitor compound, for use in treating an estrogen receptor-negative cancer.

According to this aspect, and in some embodiments, the ChEH/AEBS inhibitor compound is a selective estrogen receptor modulators (SERM) that contains a cationic aminoethoxy side chain. In some embodiments, the SERM is clomiphene, tamoxifen, 4-hydroxy-tamoxifen, raloxifene or combinations thereof. In some embodiments, the SERM is a triphenylethylene (TPE) or a derivative thereof containing a cationic aminoethoxy side chain or combinations thereof.

In another embodiment, the composition of the present invention further comprises a pharmaceutically acceptable carrier.

In some embodiments, this invention provides a method of treating cancer, comprising administering to a subject in need thereof a therapeutically effective amount of a composition as herein described. In some embodiments, the use of a ChEH/AEBS inhibitor possessing SERM activity is specifically excluded.

In some embodiments, the invention provides for the use of a therapeutically effective amount of a composition as herein described in the manufacture of a medicament for use in treating cancer.

In some embodiments, this invention provides a method of treating cancer, said method comprising administering to a subject in need thereof a therapeutically effective amount of a synergistic combination of cannabidiol (CBD) and a ChEH/AEBS inhibitor, which ChEH/AEBS inhibitor compound is not a SERM.

In some embodiments, this invention provides a method of treating cancer, said method comprising administering to a subject in need thereof a therapeutically effective amount of a synergistic combination of cannabidiol (CBD) and at least one of a naphthoquinone or a derivative thereof, or combinations thereof.

In some embodiments, according to this aspect, the cancer is cancer of the bile duct, cancer of the bladder, cancer of the bone, cancer of the bowel (including cancer of the colon and cancer of the rectum), cancer of the brain, cancer of the breast, cancer of the neuroendocrine system (commonly known as a carcinoid), cancer of the cervix, cancer of the eye, cancer of the oesophagus, cancer of the head and neck (this group includes carcinomas that start in the cells that form the lining of the mouth, nose, throat, ear or the surface layer covering the tongue), Kaposi's sarcoma, cancer of the kidney, cancer of the larynx, leukaemia: acute leukemia, chronic lymphocytic leukemia, cancer of the liver, cancer of the lung, cancer of the lymph nodes, Hodgkin's lymphoma, non-Hodgkin's lymphoma, melanoma, mesothelioma, myeloma, cancer of the ovary, cancer of the pancreas, cancer of the penis, cancer of the prostate, skin cancer, soft tissue sarcomas, cancer of the spinal cord, cancer of the stomach, testicular cancer, cancer of the thyroid, cancer of the vagina, cancer of the vulva and cancer of the uterus.

In some embodiments, this invention provides a method for treating a subject afflicted with a blood or a bone marrow related cancer in a subject in need thereof comprising administering to said subject a therapeutically effective amount of a synergistic combination of cannabidiol (CBD) and a ChEH/AEBS inhibitor, which ChEH/AEBS inhibitor compound is not a SERM.

In some embodiments, this invention provides a method for treating a subject afflicted with a blood or a bone marrow related cancer in a subject in need thereof comprising administering to said subject a therapeutically effective amount of a synergistic combination of cannabidiol (CBD) and a naphthoquinone or a derivative thereof In some embodiments, this invention provides a method for treating a subject afflicted with a blood or a bone marrow related cancer in a subject in need thereof comprising administering to said subject a therapeutically effective amount of a composition as herein described. In some embodiments, the composition comprises CBD and a ChEH/AEBS inhibitor, and in some embodiments, the composition comprises CBD and a naphthoquinone or a derivative thereof and in some embodiments, the composition comprises CBD and combinations of a ChEH/AEBS inhibitor and/or a naphthoquinone or a derivative thereof. In some embodiments, the use of a ChEH/AEBS inhibitor possessing SERM activity is specifically excluded.

In some embodiments, this invention provides a method for treating a subject afflicted with glioblastoma, in a subject in need thereof comprising administering to said subject a therapeutically effective amount of a synergistic combination of cannabidiol (CBD) and a ChEH/AEBS inhibitor. In some embodiments, the glioblastoma is estrogen receptor negative. In some embodiments, the glioblastoma is estrogen receptor positive and the ChEH/AEBS inhibitor compound is not a SERM.

In some embodiments, this invention provides a method for treating a subject afflicted with glioblastoma, in a subject in need thereof comprising administering to said subject a therapeutically effective amount of a synergistic combination of cannabidiol (CBD) and a naphthoquinone or a derivative thereof.

In some embodiments, this invention provides a method for treating a subject afflicted with glioblastoma, in a subject in need thereof comprising administering to said subject a therapeutically effective amount of a composition as herein described. In some embodiments, the use of a ChEH/AEBS inhibitor possessing SERM activity is specifically excluded.

In some embodiments, this invention provides a method for treating a subject afflicted with breast cancer, in a subject in need thereof comprising administering to said subject a therapeutically effective amount of a synergistic combination of cannabidiol (CBD) and a ChEH/AEBS inhibitor. In some embodiments, the breast cancer is estrogen receptor negative. In some embodiments, the breast cancer is estrogen receptor positive and the ChEH/AEBS inhibitor compound is not a SERM.

In some embodiments, this invention provides a method for treating a subject afflicted with breast cancer, in a subject in need thereof comprising administering to said subject a therapeutically effective amount of a synergistic combination of cannabidiol (CBD) and a naphthoquinone or a derivative thereof.

In some embodiments, this invention provides a method for treating a subject afflicted with breast cancer, in a subject in need thereof comprising administering to said subject a therapeutically effective amount of a composition as herein described. In some embodiments, the composition comprises CBD and a ChEH/AEBS inhibitor, and in some embodiments, the composition comprises CBD and a naphthoquinone or a derivative thereof and in some embodiments, the composition comprises CBD and combinations of a ChEH/AEBS inhibitor and/or a naphthoquinone or a derivative thereof. In some embodiments, the use of a ChEH/AEBS inhibitor possessing SERM activity is specifically excluded.

BRIEF DESCRIPTION OF THE DRAWINGS

FIG. 1. Graphically depicts the synergistic effect of cannabidiol with DPPE on inhibition of growth of HL-60 cell line.

FIG. 2. Graphically depicts the synergistic effect of cannabidiol with DPPE on inhibition of growth of CCRF-CEM cell line.

FIG. 3. Graphically depicts the synergistic effect of cannabidiol with 7-ketocholesterol on inhibition of growth of HL-60 cell line.

FIG. 4. Graphically depicts the synergistic effect of cannabidiol with 7-ketocholesterol on inhibition of growth of CCRF-CEM cell line.

FIG. 7. Graphically depicts the lack of synergistic effect of cannabidiol with ICI 182,780 on inhibition of growth of Hl-60 cell line.

FIG. 8. Graphically depicts the lack of synergistic effect of cannabidiol with ICI 182,780 on inhibition of growth of CCRF-CEM cell line.

FIG. 9C Graphically depicts the effect of cannabidiol on viability of MCF-7 cells incubated with different concentrations of cannabidiol and vehicle in 5% serum containing medium for 24h. Cell viability was determined by XTT assay.

FIG. 9D Graphically depicts the effect of cannabidiol on viability of A-172 cells incubated with different concentrations of cannabidiol and vehicle in 5% serum containing medium for 48h. Cell viability was determined by XTT assay.

FIG. 11A Graphically depicts the effect of tamoxifen on viability of HL-60 cells incubated with different concentrations of tamoxifen and vehicle in 5% serum containing medium for 24h. FIG. 11B Graphically depicts the effect of tamoxifen on viability of CCRF cells incubated with different concentrations of tamoxifen and vehicle in 5% serum containing medium for 24h.

FIG. 11C Graphically depicts the effect of tamoxifen on viability of MCF-7 cells incubated with different concentrations of tamoxifen and vehicle in 5% serum containing medium for 24h. Cell viability was determined by XTT assay.

FIG. 12A graphically depicts the synergistic effect of cannabidiol with clomiphene, tamoxifen and menadione (Mena) on growth inhibition of HL-60 cells incubated with different concentrations of cannabidiol, clomiphene and vehicle in 5% FCS medium for 24h.

FIG. 12B graphically depicts the synergistic effect of cannabidiol with clomiphene, tamoxifen and menadione (Mena) on growth inhibition of HL-60 cells incubated with different concentrations of cannabidiol, tamoxifen and vehicle in 5% FCS medium for 24h of HL-60 cells incubated with different concentrations of cannabidiol, tamoxifen and vehicle in 5% FCS medium for 24h.

FIG. 14A graphically depicts the synergistic effect of cannabidiol with clomiphene and tamoxifen, on growth inhibition of CCRF-CEM cells incubated with different concentrations of cannabidiol, clomiphene and vehicle in 5% FCS medium for 24h. Cell viability was determined by XTT assay.

FIG. 14B graphically depicts the synergistic effect of cannabidiol with clomiphene and tamoxifen, on growth inhibition of CCRF-CEM cells incubated with different concentrations of cannabidiol, tamoxifen and vehicle in 5% FCS medium for 24h.

FIG. 16 graphically depicts the synergistic effect of cannabidiol with tamoxifen, on growth inhibition of MCF-7 cell line. The A-172 cells were incubated with different concentrations of cannabidiol, clomiphene and vehicle in 5% FCS medium for 48h. Cell viability was determined by XTT assay.

FIG. 17A graphically depicts the induction of apoptosis in HL-60 cells by cannabidiol, clomipheneand menadione. Dose-response effect of cannabidiol, clomiphene and menadioneon induction of apoptosis in HL-60 cells incubated with cannabidioland vehicle in 5% FCS medium for 24 and 48h is shown.

FIG. 17B graphically depicts the induction of apoptosis in HL-60 cells by cannabidiol, clomipheneand menadione. Dose-response effect of cannabidiol, clomiphene and menadioneon induction of apoptosis in HL-60 cells were incubated with cannabidiol, clomiphene and vehicle in 5% FCS medium for 24h is shown.

FIG. 17C graphically depicts the induction of apoptosis in HL-60 cells by cannabidiol, clomipheneand menadione. Dose-response effect of cannabidiol, clomiphene and menadioneon induction of apoptosis in HL-60 cells were incubated with cannabidiol, menadione and vehiclein 5% FCS medium for 24h is shown.

FIG. 18A graphically depicts the induction of apoptosis in CCRF-CEM cells by cannabidiol, clomiphene and tamoxifen in CCRF-CEM cells incubated with cannabidiol and vehiclein serum free and 5% FCS medium for 24h.

FIG. 18B graphically depicts the induction of apoptosis in CCRF-CEM cells by cannabidiol, clomiphene and tamoxifen in CCRF-CEM cells incubated with cannabidiol, clomiphene and vehiclein 5% FCS medium for 24h.

FIG. 21B depicts the effect of cannabidiol, clomiphene and cannabidiol+clomiphene on tumor volume in a mouse xenograft model transplanted with HL-60 cells, where tumors were harvested and the representative images of tumors in each group are shown.

DETAILED DESCRIPTION OF THE INVENTION

Figure 5:
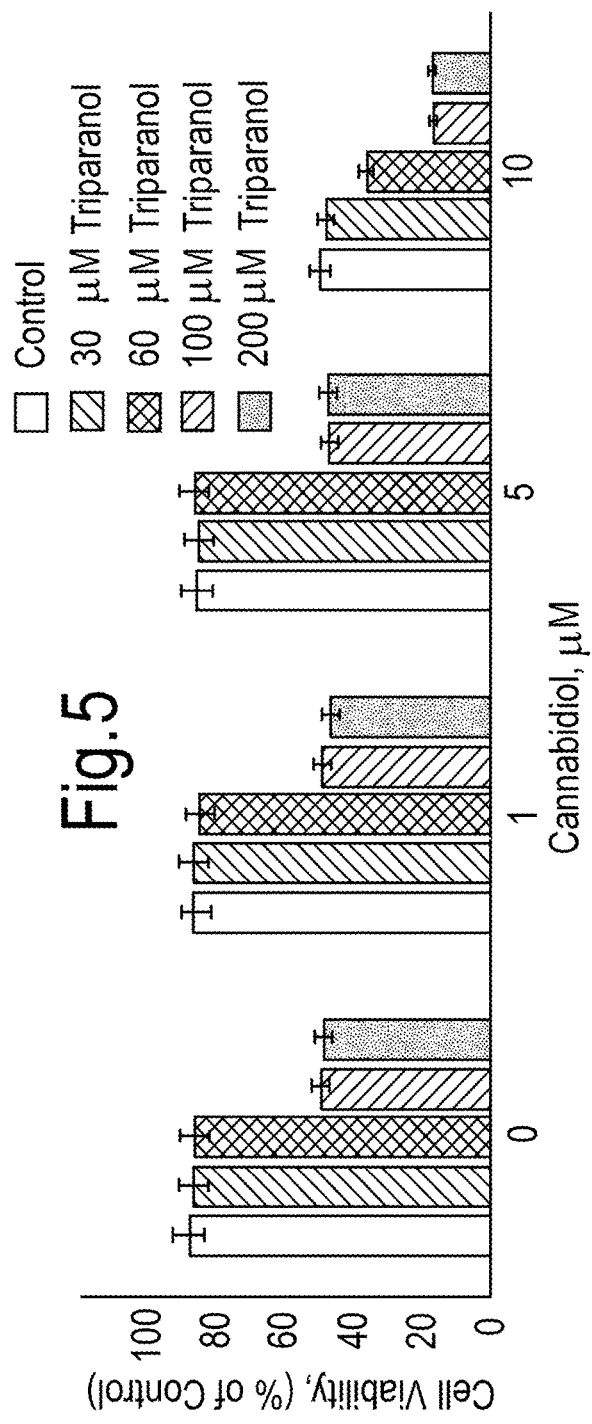
FIG. 5. Graphically depicts the synergistic effect of cannabidiol with triparanol on inhibition of growth of Hl-60 cell line.

In one embodiment, the present invention is a composition comprising cannabidiol (CBD) and at least one ChEH/AEBS inhibitor effective in the treatment of malignancies such as, but not limited to blood cancer, bone marrow related cancer, breast cancer and glioblastoma.

This invention provides a composition comprising cannabidiol (CBD) and at least one naphthoquinone or a derivative thereof effective in the treatment of malignancies such as, but not limited to blood cancer, bone marrow related cancer, breast cancer and glioblastoma.

The term "cannabidiol" (CBD) as used herein refers to a phyto-cannabinoid produced from the plat Cannabis species. In some embodiments CBD used in the present invention is in a purified form. In other embodiments, CBD is a component of a plant extract. In some embodiments, a plant extract comprises at least 10% to 95% CBD. In some embodiments, a plant extract comprises at least 20% to 80% CBD. In some embodiments, a plant extract comprises at least 30% to 70% CBD. In some embodiments, a plant extract comprises at least 40% to 60% CBD.

In another embodiment, CBD is a botanical drug substance (BDS). A "botanical drug substance" or "BDS" is defined in the Guidance for Industry Botanical Drug Products Draft Guidance, August 2000, US Department of Health and Human Services, Food and Drug Administration Centre for Drug Evaluation and Research as: "A drug derived from one or more plants, algae, or microscopic fungi. It is prepared from botanical raw materials by one or more of the following processes: pulverisation, decoction, expression, aqueous extraction, ethanolic extraction or other similar processes." A botanical drug substance does not include a highly purified or chemically modified substance derived from natural sources.

In another embodiment, where a synthetic CBD is used the term is intended to include compounds, metabolites or derivatives thereof, and pharmaceutically acceptable salts of CBD.

In another embodiment, the composition of the present invention comprises chemically-modified derivatives of fully-decarboxylated CBD which retain desired activity, or more preferably natural derivatives exhibiting improved activity which are produced according to standard principles of medicinal chemistry. In some embodiments, fully-decarboxylated CBD derivatives may exhibit a lesser degree of activity than the starting material so long as they retain sufficient activity to be therapeutically effective or exhibit improvements in properties desirable in pharmaceutically active agents such as improved solubility, enhanced uptake or reduced toxicity.

In another embodiment, the composition of the present invention comprises a naphthoquinone or a derivative thereof. Naphthoquinones are a class of organic compounds derived from naphthalene. Non-limiting examples of naphthoquinones are: 1,2-Naphthoquinone, 1,4-Naphthoquinone, menadione, 2,6-Naphthoquinone, Hexahydroxy-1,4-naphthalenedione, 5-hydroxy-1,4-naphthalenedione, 2-Methoxy-1,4-naphthoquinone, Pentahydroxy-1,4-naphthalenedione and 2,3,5,7-Tetrahydroxy-1,4-naphthalenedione.

The term "ChEH/AEBS inhibitor" as used herein refers to compounds as herein described, and as known in the art to be identified as same.

In some aspects, the ChEH/AEBS inhibitors comprise different pharmacological classes of natural or synthetic compounds. Cholesterol epoxide hydrolase (ChEH) catalyzes the hydration of cholesterol-5,6-epoxides (5,6-EC) into cholestane-3β,5α,6β-triol. ChEH is a hetero-oligomeric complex called the microsomal anti-estrogen binding site (AEBS) comprising 3bhydroxysterol-D8-D7-isomerase (D8D7I) and 3b-hydroxysterol-D7-reductase (DHCR7). D8D7I and DHCR7 regulate cholesterol biosynthesis and tumor cells growth differentiation, death and cancer progression.

ChEH/AEBS inhibitors comprise a number of compounds, including, inter alia, tesmilifene (DPPE, N,N0-diethylamino-4-(phenylmethylphenoxy)-ethanamine,HCl)3 PBPE, PCPE, MBPE, MCPE, PCOPE, MCOPE, MCOCH2PE. sigma receptor ligands such as SR31747A, BD10008 Haloperidol, SR-31747A, Ibogaine, AC-915, Rimcazole, Trifluoroperazine, Amiodarone, cholesterol biosynthesis inhibitors such as Triparanol, Terbinafine, U-18666A, Ro 48-8071, AY9944, SKF-525A, unsaturated fatty acids such as oleic acid, a-linolenic acid, acidarachidonic acid (ARA), docosahexaenoic acid (DHA), ring B oxysterols such as 6-Ketocholestanol, 7-Ketocholestanol, 7-Ketocholesterol, 7α-hydroxycholesterol, 7β-Hydroxycholesterol, 6-Keto-5 hydroxycholestanol Cholestane-3β,5α,6β-triol(CT) and others as will be appreciated by the skilled artisan (see for example, Silvente-Poirot S, Poirot M. Cholesterol epoxide hydrolase and cancer. Current opinion in pharmacology. 2012; 12(6):696-703; de Medina P, Paillasse M R, Segala G, Poirot M, Silvente-Poirot S:Identification and pharmacological characterization of cholesterol-5,6-epoxide hydrolase as a target for tamoxifen and AEBS ligands. Proc Natl Acad Sci USA 2010, 107:13520-13525, all of which are hereby incorporated in their entirety by reference herein).

In some aspects, in particular, with reference for compositions, methods and uses for treating estrogen receptor negative cancer, the ChEH/AEBS inhibitors comprise a triphenylethylene (TPE) derivative such as the antiestrogens (AEs) clomiphene (CL) and tamoxifen (Tam).

In another embodiment, the term "cancer" is blood cancer. In another embodiment, the term "cancer" is bone marrow cancer or bone marrow related cancer. In another embodiment, the term "cancer" is breast cancer. In another embodiment, the term "cancer" is glioblastoma. In another embodiment, blood cancer is leukemia. In another embodiment, blood cancer is acute promyelocytic leukemia (AML). In another embodiment, blood cancer is myeloblastic leukemia. In another embodiment, blood cancer is Non-Hodgkin's lymphoma. In another embodiment, blood cancer is Myeloma. In another embodiment, blood cancer is lymphoma. In another embodiment, bone marrow cancer is a Myeloproliferative disorder.

In some embodiments, the composition of the present invention is used for treating a subject afflicted with cancer. In some embodiments, treating a subject afflicted with cancer using the composition of the present invention induces a synergistic effect as compared to the combined effect of using each of the compounds alone. A synergistic effect is a coordinated or correlated action of two or more compounds, so that the combined action is greater than the sum of each compound acting separately. Non-limiting examples of compounds of the present invention that have a synergistic effect when co-administered with CBD are DPPE, 7-ketocholesterol, triparanol, or combinations thereof. In some embodiments, the non-limiting examples of compounds of the present invention that have a synergistic effect when co-administered with CBD in estrogen receptor negative cancers include triphenylethylene (TPE) derivatives such as the antiestrogens (AEs) clomiphene (CL) and tamoxifen (Tam). In some embodiments, the synergistic effect when co-administered with CBD includes the naphthoquinone derivative menadione.

In other embodiments, treating a subject afflicted with cancer with a combination of CBD and ChEH/AEBS inhibitors and/or a naphthoquinone or a derivative thereof induces more than an additive effect as compared to the combined effect of administration of each of the compounds alone. The term additive effect means that the combined action of two or more compounds is equal to the sum of each compound acting separately.

Referring to Example 1, and FIGS. 1-6, representative ChEH/AEBS inhibitors were demonstrated to possess anti-cancer activity, whether selective ChEH/AEBS inhibitors (DPPE) or, for example, ring B oxysterols (7-ketocholesterol) or a cholesterol biosynthesis class of inhibitors (triparanol) was used, when used in combination with CBD, demonstrating true synergistic effect.

Referring to Example 2, a representative naphthoquinone or a derivative thereof, menadione was shown to possess anti-cancer activity, as well, when used in combination with CBD, demonstrating true synergistic effect.

Figure 13:
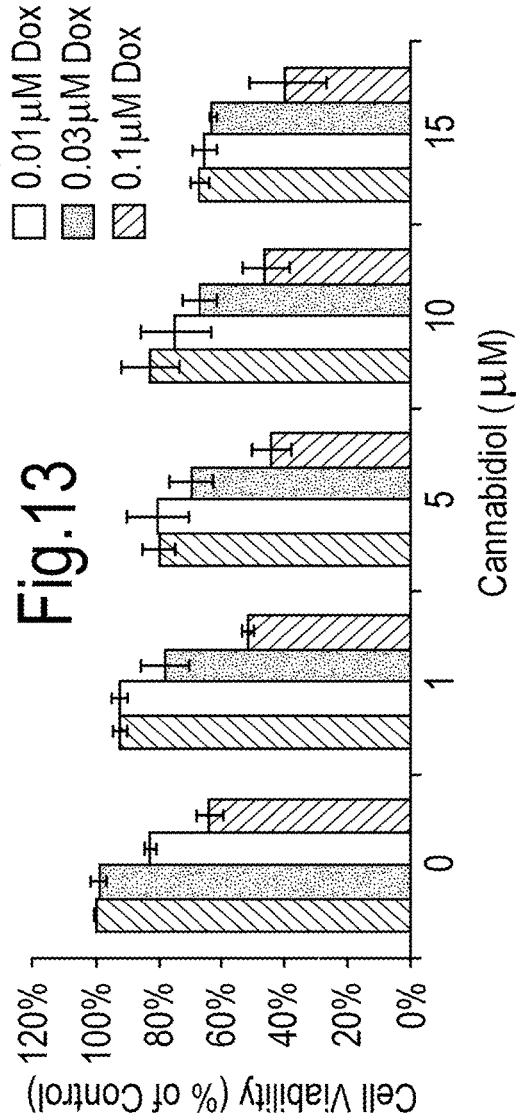
FIG. 13 graphically depicts the additive effect of cannabidiol with doxorubicin on growth inhibition of HL-60 cells incubated with different concentrations of cannabidiol, doxorubicin (Dox) and vehicle in 5 and 10% FCS medium for 24h. Cell viability was determined by XTT assay.

Examples of additional compounds that have an additive effect when co-administered with CBD are doxorubicin and anthracyline as shown in FIG. 13.

In some embodiments, the synergistic effect of the composition of the present invention in treating cancer is at least 1.1 fold higher, than the additive effect in treating cancer by administering the compounds of the same composition separately.

In some embodiments, the synergistic effect in treating cancer using the composition of the present invention is between 1.1 fold to 2 fold higher, 2 fold to 3 fold higher, 3 fold to 4 fold higher, 4 fold to 5 fold higher than the additive effect in treating cancer by administering the compounds of the same composition separately.

In some embodiments, the synergistic effect in treating cancer using the composition of the present invention is more than 5 fold higher than the additive effect in treating cancer by administering the compounds of the same composition separately.

In some embodiments, the composition of the present invention is a combination of CBD and an ChEH/AEBS inhibitors, wherein the molar ratio of the CBD to the ChEH/AEBS inhibitors is between 50:1 to 1:50 (CBD: the ChEH/AEBS inhibitors). In some embodiments, the composition of the present invention is a combination of CBD and a naphthoquinone or a derivative thereof, wherein the molar ratio of the CBD to the naphthoquinone or a derivative thereof is between 50:1 to 1:50 (CBD: the naphthoquinone or a derivative thereof).

In some embodiments, the composition of the present invention is a combination of CBD and an ChEH/AEBS inhibitors, wherein the molar ratio of the CBD to ChEH/AEBS inhibitors is between 30:1 to 1:30 (CBD: ChEH/AEBS inhibitors).

In some embodiments, the composition of the present invention is a combination of CBD and a naphthoquinone or a derivative thereof, wherein the molar ratio of the CBD to the naphthoquinone or a derivative thereof is between 30:1 to 1:30 (CBD: the naphthoquinone or a derivative thereof).

In some embodiments, the composition of the present invention is a combination of CBD and an ChEH/AEBS inhibitors, wherein the molar ratio of the CBD to ChEH/AEBS inhibitors is between 10:1 to 1:10 (CBD: ChEH/AEBS inhibitors).

In some embodiments, the composition of the present invention is a combination of CBD and a naphthoquinone or a derivative thereof, wherein the molar ratio of the CBD to the naphthoquinone or a derivative thereof is between 10:1 to 1:10 (CBD: the naphthoquinone or a derivative thereof).

In some embodiments, the composition of the present invention is a combination of CBD and an ChEH/AEBS inhibitors, wherein the molar ratio of the CBD to naphthoquinone is between 5:1 to 1:5 (CBD: ChEH/AEBS inhibitors).

In some embodiments, the composition of the present invention is a combination of CBD and a naphthoquinone or a derivative thereof, wherein the molar ratio of the CBD to the naphthoquinone or a derivative thereof is between 5:1 to 1:5 (CBD: the naphthoquinone or a derivative thereof).

In some embodiments, the composition of the present invention is a combination of CBD and an ChEH/AEBS inhibitors, wherein the molar ratio of the CBD to ChEH/AEBS inhibitors is between 2:1 to 1:2 (CBD: ChEH/AEBS inhibitors).

In some embodiments, the composition of the present invention is a combination of CBD and a naphthoquinone or a derivative thereof, wherein the molar ratio of the CBD to the naphthoquinone or a derivative thereof is between 2:1 to 1:2 (CBD: the naphthoquinone or a derivative thereof).

In some embodiments, the composition of the present invention is a combination of CBD and an ChEH/AEBS inhibitor, wherein the molar ratio of the CBD to ChEH/AEBS inhibitors is 1:1 (CBD: ChEH/AEBS inhibitors).

In some embodiments, the composition of the present invention is a combination of CBD and a naphthoquinone or a derivative thereof, wherein the molar ratio of the CBD to the naphthoquinone or a derivative thereof is 1:1 (CBD: the naphthoquinone or a derivative thereof).

In another embodiment, the composition of the present invention is formulated as a pharmaceutical composition further comprising one or more pharmaceutically acceptable carriers, expedients or diluents.

In some embodiments, the term "treatment"" as used herein refers to any response to, or anticipation of, a medical condition in a mammal, particularly a human, and includes but is not limited to: not be predisposed to the condition, but has not yet, been diagnosed with the condition and, inhibiting the medical condition, e.g., arresting, slowing or delaying the onset, development or progression of the medical condition; or relieving the medical condition, e.g., causing regression of the medical condition or reducing the symptoms of the medical condition.

In another embodiment, the term "subject" refers to a human afflicted with cancer. In another embodiment, the term "subject" refers to a mammal such as a pet or a farm animal afflicted with cancer.

In another embodiment, the term "administering" as used herein, includes delivery of a composition or one or more pharmaceutically active ingredients to a subject, by any appropriate methods, which serve to deliver the composition or its active ingredients or other pharmaceutically active ingredients to the subject. In another embodiment, the method of administration may vary depending on various factors, such as for example, the components of the pharmaceutical composition or the nature of the pharmaceutically active or inert ingredients, the site of the potential or actual malady, age and physical condition of the subject. Some non-limiting examples of ways to administer the composition of the present invention to a subject include: oral, intravenous, topical, intrarespiratory, intraperitoneal, intramuscular, parenteral, sublingual, transdermal, intranasal, aerosol, intraocular, intratracheal, intrarectal, vaginal, dermal patch, eye drop, ear drop or mouthwash.

As used herein, "therapeutically effective amount" refers to administration of an amount of the composition of the present invention, to a subject in need thereof that achieves prevention, inhibition or regression of the cancer in the subject in need thereof.

In some embodiments, the amount of CBD in the composition administered to the subject is between 0.1 mg/kg (body weight)/day and 50 mg/kg (body weight)/day. In some embodiments, the amount of CBD in the composition of the present invention is between 10 mg/kg (body weight)/day and 1000 mg/kg (body weight)/day. In some embodiments, the amount of CBD in the composition of the present invention is between 50 mg/kg (body weight)/day and 500 mg/kg (body weight)/day. In some embodiments, the amount of CBD in the composition of the present invention is between 500 mg/kg (body weight)/day and 2000 mg/kg (body weight)/day.

In some embodiments, the amount of ChEH/AEBS inhibitor or inhibitors, or the amount of naphthoquinone or a derivative thereof in the composition administered to the subject is between 0.1 mg/kg (body weight)/day and 50 mg/kg (body weight)/day. In some embodiments, the amount of ChEH/AEBS inhibitor or inhibitors, or the amount of naphthoquinone or a derivative thereof in the composition of the present invention is between 10 mg/kg (body weight)/day and 1000 mg/kg (body weight)/day. In some embodiments, the amount of ChEH/AEBS inhibitor or inhibitors, or the amount of naphthoquinone or a derivative thereof in the composition of the present invention is between 50 mg/kg (body weight)/day and 500 mg/kg (body weight)/day. In some embodiments, the amount of ChEH/ AEBS inhibitor or inhibitors, or the amount of naphthoquinone or a derivative thereof in the composition of the present invention is between 500 mg/kg (body weight)/day and 2000 mg/kg (body weight)/day.

In another embodiment, the duration of the treatment is between 24h to 14 days. In another embodiment, the duration of the treatment is between 24h to 30 days. In another embodiment, the duration of the treatment is between 1 to 12 months. In another embodiment, the method is used to treat a subject with a chronic cancer and the duration of the treatment is for the life time of the subject.

In some embodiments, administration of the composition of the present invention to a subject afflicted with cancer induces apoptosis of a cancerous cell thereby treating the subject. Apoptosis of cancer cells is quantified by methods known in the art such as, but no limited to the XTT assay described below in the materials and methods section.

In some embodiments, administration of the composition of the present invention to a subject afflicted with cancer suppresses tumor growth thereby treating the subject. In some embodiments, suppression of tumor growth refers to the slowing or prevention of growth in the size of a tumor after administration of the composition of the present invention. In some embodiments, tumor growth is compared to relevant clinical data of the treated cancer as known in the art. In some embodiments, tumor growth is compared to pre-treatment tumor size and/or volume of the treated subject. Measurement of the size of a tumor is done by methods known in the art.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272, 057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference. Other general references are provided throughout this document.

Materials and Methods

Reagents:

Reagents were purchased from commercial vendors, dissolved in 100% DMSO and stored at −20° C. The final DMSO concentration was 0.1%. Acridine orange/ethidium bromide stain was prepared at a concentration of 1 mg/ml in PBS. XTT and all other chemicals were acquired from Sigma (St. Louis, Mo.). Control cultures contained the vehicle, which had no effect by itself.

Cell Culture:

human HL-60, myeloblastic leukemia and CCRF-CEM, acute lymphoblastic leukemia cell line were cultured in RPMI-1640 supplemented with 10% (v/v) heat-inactivated fetal calf serum, 2 mM L-glutamine, 100U/ml penicillin and 100 µg/ml streptomycin. MCF-7, breast cancer and A-172, glioblastoma cell lines were cultured in DMEM supplemented with 10% (v/v) heat-inactivated fetal calf serum, 2 mM L-glutamine, 100U/ml penicillin and 100 µg/ml streptomycin. Cultures were maintained at 37° C. in a humidified atmosphere with 5% CO2 and maintained in exponential phase by transfer to fresh medium every 2-3 days. Experiments were conducted in serum free medium and 5% or 10% FCS medium. The trypanblue dye exclusion method [17] was used for cell counting performed using a hemocytometer under light microscope.

Determination of Cell Viability:

cell viability analysis of HL-60, CCRF-CEM, A-172 and MCF-7 cells was assessed by their (2,3 [-bis-2-methoxy-4-nitro-5-sulphophenyl]-2H-tetrazolium-5-carboxianilide, inner salt (XTT) reduction activity. 100 µl of $2.5 \times 10^5$ cells/ml was incubated with treatments at the indicated time. At the end of the incubation period, 25 µl of 1 mg·ml XTT solution (containing 0.2 mM phenazinemethosulphate (PMS) was added and the cells were incubated for an additional 1h. The OD values were measured using an ELISA reader at 450 nm with a reference wavelength of 650 nm. Data were expressed as the mean percentage of the three replicates, normalized to the untreated vehicle.

Morphological Quantification of Apoptosis:

for determination of apoptosis, cells were harvested (650 g, 7 min) and stained with acridine orange/ethidium bromide at a final concentration of 0.05 mg/ml. This method allows distinguishing between live, necrotic and apoptotic cells (FIG. 11). Cells were scored as alive if their nuclei exhibited normal morphology and were green. Cells exhibiting normal morphology and orange color were indicated as necrotic. Cells were scored as apoptotic if their nuclei exhibited condensation of the chromatin and/or nuclear fragmentation. At least 100 cells were counted under a fluorescence microscope and the percentage of affected cells was calculated.

Western Blot Analysis:

for Western blot analysis, 5×10⁷ cells/ml was treated with and without 20 µM CBD and 20 µM clomiphene (CL) for the indicated periods of time. Cells washed twice with ice cold PBS and lysed in RIPA buffer (50 mM Tris-HCl, 0.1% NP-40, 1 mM DTT, 0.25M sucrose, 2 mM $MgCl_2$, pH 7.4) for 30 min on ice. After centrifugation, the post-nuclear supernatant containing the cell soluble fraction were loaded on to a 12% SDS-PAGE gel. After electrophoresis, the gels were blotted onto a PVDF membrane (Bio-Rad, Hercules, Calif.), blocked with 5% (w/v) milk for overnight at 4° C. temperature, washed briefly in Tris-Buffered Saline Tween-20 (TBST), and then probed overnight at 4° C. with the anti-mouse human anti-MC1-1 and calreticulin (CRN) primary antibodies. Primary antibody binding was detected with anti-mouse IgG conjugated to horseradish peroxidase (Jackson Immunoresearch, Avondale, Pa.), and made visible by enhanced chemiluminescence (ECL) (Biological Industries, Israel), according to manufacturer's instructions. Antibodies against MCl-1 and calreticulin (CRN) were purchased from Santa Cruz, Calif., USA.

In Vivo Anti-Tumor Efficacy of CBD and CL:

NOD/SCID mice were bred and housed at animal facility of Ben-Gurion University of the Negev, Israel. All animals were used between 7-8 weeks old of age. For induction of tumor, mice were irradiated with 2.7 Gy X ray radiation for 2 min. The following 5 hours, mice were injected with 1 million viable HL-60 cells on right flank of mice. Mice were monitored for tumorigenesis. Tumors were measured during 14 days and their volumes (mm³) were calculated as $(d^2 X D)/2$ (where d is the shortest and D is the longest diameter of the tumor in mm). Following the day mice were divided into four groups (6 mice/group): vehicle (veh), cannabidiol group (CBD group), clomiphene (CL group), and combination (CBD+CL group). The mice were injected peritumorally with 5 mg CBD/kg for CBD group, 10 mg CL/kg for CL group and 5 mg CBD+10 mg CL for CBD+CL group (dissolved in 0.1 ml of sterile PBS supplemented with 5 mg/ml defatted and dialyzed bovine serum albumin) or its vehicle. The injection was repeated once a day, 5 days per week, and tumor volumes were checked twice a week until the vehicle died and the remained animals were sacrificed.

Data Presentation and Statistical Analysis:

Viability experiments were performed in triplicates and experiments were repeated at least two or three times. Where statistical analysis was performed, same was evaluated by Students t-test. Some of the data is presented in the FIGS. provided, with statistically significant differences designated as $*p<0.05$, $**p<0.01$.

Example 1

Combinations of Cannabidiol and ChEH/AEBS Inhibitors Cause a Reduction in Cancer Cell Viability The effect of combinations of cannabidiol and ChEH/AEBS inhibitors—exposure on the viability of HL-60 and CCRF-CEM, A-172 and MCF-7 cell lines in vitro was examined. To this end, the tumor cells were cultured in 10% FCS supplemented medium and exposed to various concentrations of cannabidiol (1, 5, 10, and 30 µM) for 48h in 5% FCS containing medium and 1, 5, 10 and 30 µM ChEH/AEBS inhibitors (FIGS. 1, 2, 3 and 4).

With regard to the HL-60 assays, the results showed that exposure to cannabidiol at concentrations of even 1 µM or more when in combination with ChEH/AEBS inhibitors for 48 h treatment led to a significant reduction in the number of viable cells. The reduction in cell viability was dose responsive having a profound effect on reduction of cell viability even at very low concentrations 1 µM or 5 µM.

Similarly, results of the combination of exposure to cannabidiol at concentrations of even 1 µM or more when in combination with ChEH/AEBS inhibitors in the estrogen receptor deficient CCRF-CEM cell line showed a significant reduction in the number of viable cells. The reduction in cell viability was dose responsive having a profound effect on reduction of cell viability even at very low concentrations 1 µM or 5 µM of each.

These results demonstrate that representative ChEH/AEBS inhibitors, whether selective inhibitors (DPPE) or, for example, ring B oxysterols (7-ketocholesterol), when provided in combination with CBD exhibit potent anticancer activity.

Figure 6:
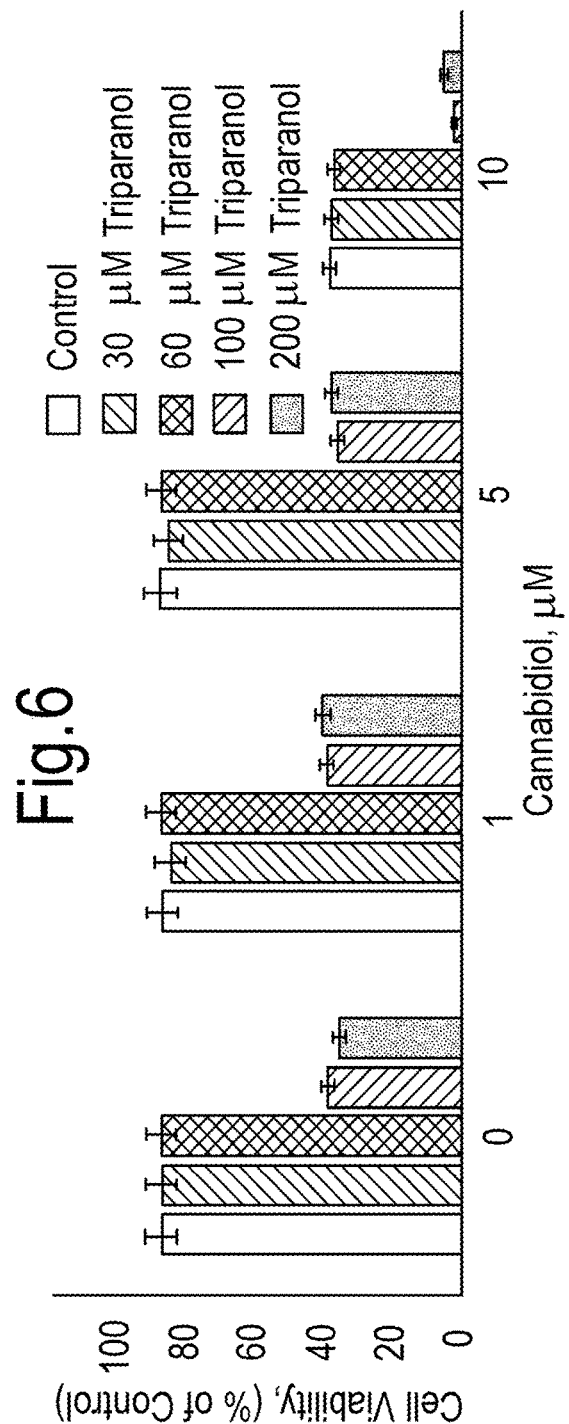
FIG. 6. Graphically depicts the synergistic effect of cannabidiol with triparanol on inhibition of growth of CCRF-CEM cell line.
Figure 9A:
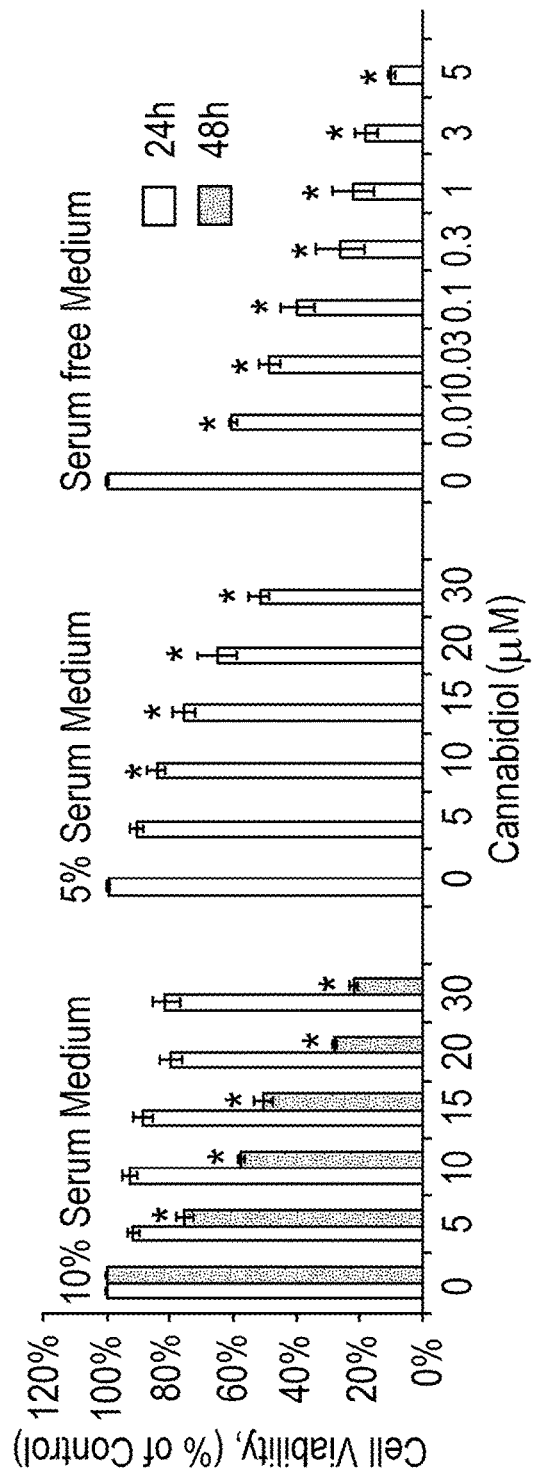
FIG. 9A Graphically depicts the effect of cannabidiol on viability of HL-60 cells incubated with different concentrations of cannabidiol and vehicle in 5% FCS serum and serum free medium for 24h, 10% FCS medium for 24 and 48h.
Figure 9B:
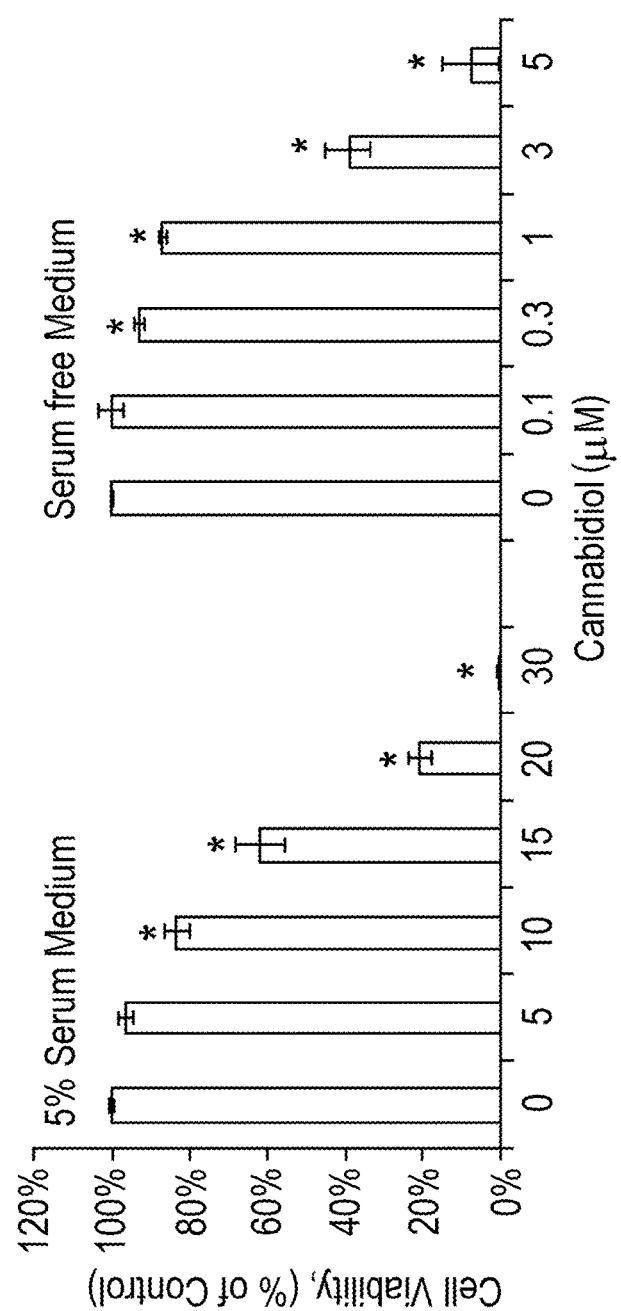
FIG. 9B Graphically depicts the effect of cannabidiol on viability of CCRF-CEM cells incubated with different concentrations of cannabidiol and vehicle in serum free and 5% serum containing medium for 24h.

To further elaborate on the fact that CBD combination therapy with broad ChEH/AEBS inhibitor use is effective, another representative ChEH/AEBS inhibitor was evaluated for its activity in combination with CBD against HL-60 and CCRF-CEM viability (FIGS. 5 and 6). In this case, an ChEH/AEBS inhibitor of the cholesterol biosynthesis class of inhibitors (triparanol) was selected and used in concentrations of 30, 60, 100 and 200 µM. Although higher concentrations of the triparanol were evaluated nonetheless, a significant reduction in the number of viable cells, with the optimum triparanol concentration of 10 µM with 1-10 µM of CBD.

FIGS. 7 and 8 provide the results of the negative control for these studies, combination therapy of CBD and with ICI-182,780 (1, 5, 10 and 30 µM) a non cationic antiestrogen whose combination with CBD provides no added benefit.

Thus, representative classes of ChEH/AEBS inhibitors when provided as a combination therapy with CBD exhibited profound anti-cancer activity.

Example 2

Cannabidiol, TPEs (Clomiphene and Tamoxifen) and Menadione Cause a Reduction in Cell Viability The effect of cannabidiol-exposure on the viability of HL-60 and CCRF-CEM, A-172 and MCF-7 cell lines in vitro was examined. To this end, the tumor cells were cultured in 10% FCS supplemented medium and exposed to various concentrations of cannabidiol (5, 10, 15, 20 and 30 µM) for 24 h and 48h in 10% or 5% FCS containing medium and 0.01, 0.03, 0.1, 0.3, 1, 3 and 5 µM CBD for 24 h in serum free medium (FIGS. 9A, 9B, 9C and 9D). The results showed that exposure to cannabidiol at concentrations of 5 µM or more for 24h and 48 h treatment led to a significant reduction in the number of viable cells (FIGS. 9A, 9B, 9C and 9D). The reduction in cell viability was dose responsive both at 24 and 48 hr exposure (FIGS. 9A, 9B, 9C and 9D). CBD had a profound effect on reduction of cell viability even at very low concentration 0.2 µM in serum free condition for 24h of exposure. $IC_{50}$ value was obtained in 10% FCS medium after 48 h as 16 µM. With decreased serum concentration (5% FCS) in the medium, $IC_{50}$ was also obtained in 24h. In serum free medium $IC_{50}$ was 0.26 µM for 24h. In 10% FCS medium cells proved to be less sensitive to CBD for 24h. The statistical significance of cell viability reduction was $P<0.05$.

Figure 10A:
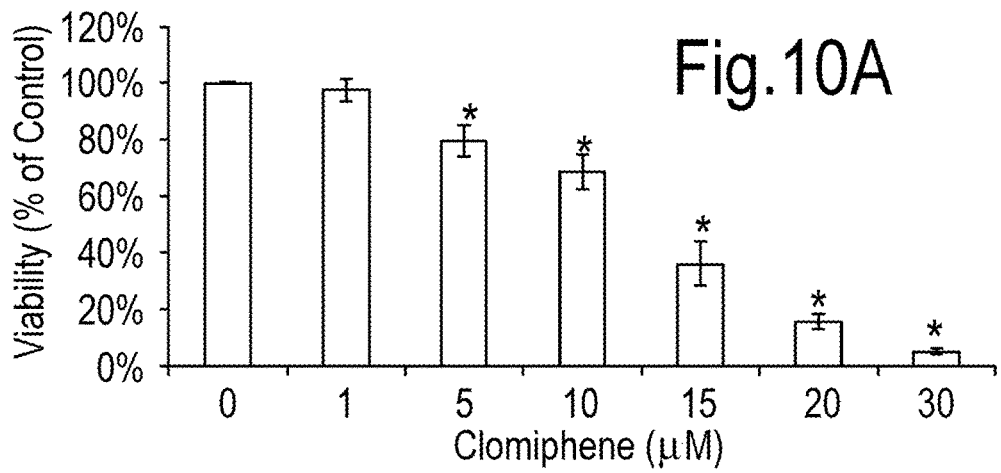
FIG. 10A Graphically depicts the effect of clomiphene on viability of HL-60 cells incubated with different concentrations of clomiphene and vehicle in 5% serum containing medium for 24h. Cell viability was determined by XTT assay.
Figure 10B:
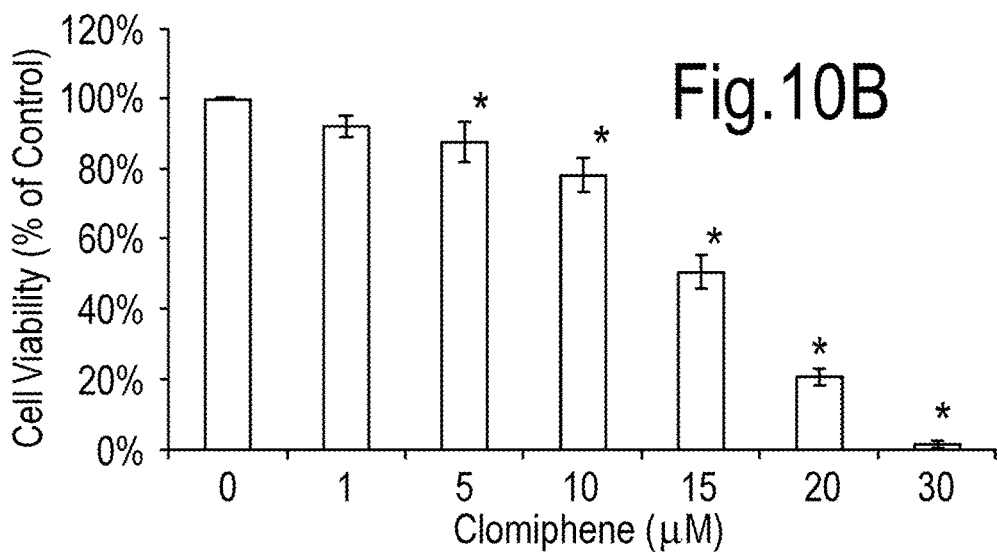
FIG. 10B Graphically depicts the effect of clomiphene on viability of CCRF cells incubated with different concentrations of clomiphene and vehicle in 5% serum containing medium for 24h. Cell viability was determined by XTT assay.
Figure 10C:
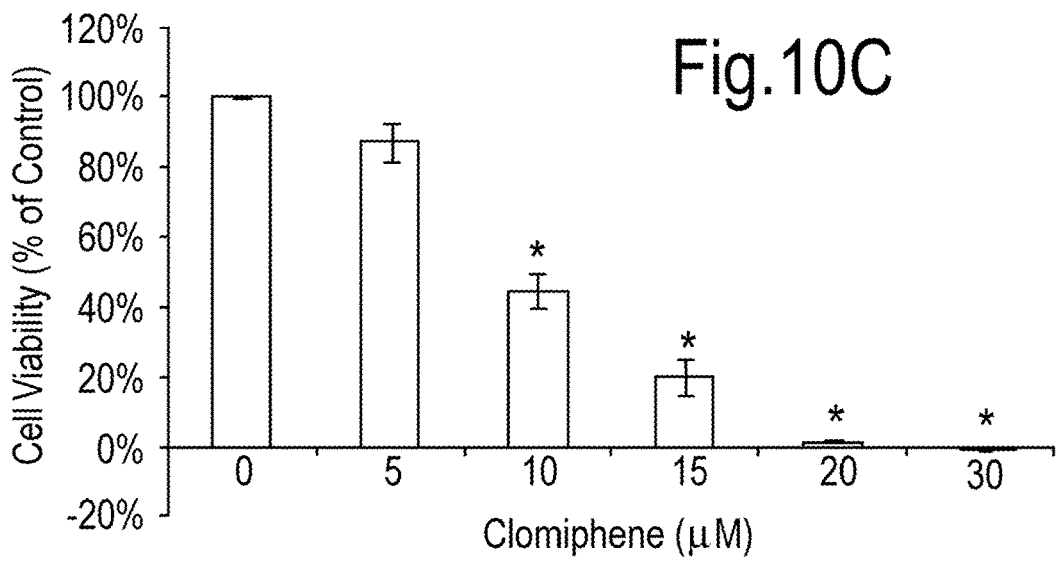
FIG. 10C Graphically depicts the effect of clomiphene on viability of A-172 cells were incubated with different concentrations of clomiphene and vehicle in 5% serum containing medium for 48h. Cell viability was determined by XTT assay.

The effect of clomiphene and tamoxifen on HL-60, CCRF-CEM, A-172 and MCF-7 cell lines was also examined. To this end the dose dependent reduction in cell viability was observed with clomiphene in 5% serum supplemented medium for 24h, for HL-60, CCRF-CEM and 48 hr for A-172 cell line (FIGS. 10 and 11). The IC 50 values for clomiphene in HL-60, A-172 and CCRF-CEM cell lines were found to be 14, 11 and 15 µM respectively. The IC 50 values of tamoxifen for HL-60, CCRF-CEM and MCF-7 was found to be 12, 16 and 12 µM respectively.

Example 3

Synergistic Effect of CBD with TPE and Naphthoquinone

Figure 12C:
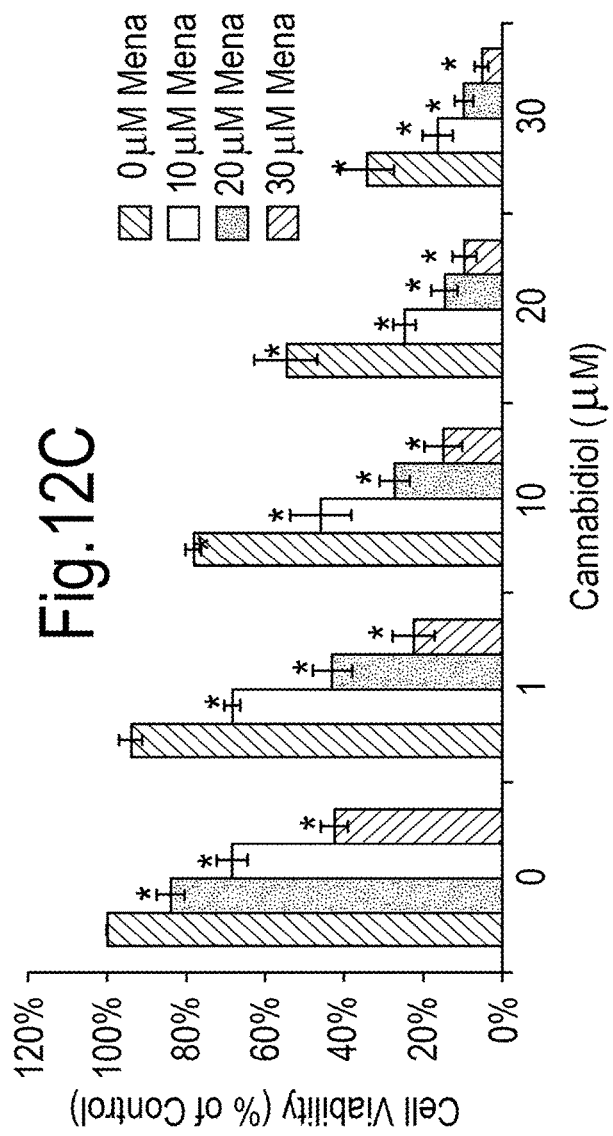
FIG. 12C graphically depicts the synergistic effect of cannabidiol with clomiphene, tamoxifen and menadione (Mena) on growth inhibition of CCRF cells incubated with different concentrations of cannabidiol, menadione and vehicle in 5% FCS medium for 24h. Cell viability was determined by XTT assay.

In this study, CBD had synergistic anticancer effects with clomiphene, tamoxifen and menadione (FIG. 12 A, B, C). As shown in FIG. 4 the combination CBD, clomiphene, tamoxifen and menadione effectively reduced the viability of HL-60 cells. The most effective combinations were found as 5 µM CBD and 15 µM clomiphene (FIG. 12A), 10 µM CBD and 10 µM tamoxifen (FIG. 12B). Menadione and CBD showed more than additive in reducing the cell viability at high concentration of menadione (FIG. 12C). Conventional chemotherapeutic drug anthracycline, doxorubicin showed additive effect with CBD in reduction in viability of HL-60 cells (FIG. 13).

The effect of CBD and TPE (clomiphene and tamoxifen) in estrogen receptor (ER) negative cell lines CCRF-CEM, A-172 and ER positive cell line MCF-7 was examined. As shown in FIGS. 14A and B CBD with TPEs caused synergistic reduction in the viability of CCRF-CEM cells similarly to HL-60 cell line. This finding supports the notion that the cannabidiol and TPE interact independently of ER involvement in reduction of cell viability mechanism. The most potent combination was found as 10 µM CBD and 10 µM tamoxifen which synergistically reduced the viability of MCF-7 cells (FIG. 15). The human glioblastoma cell line, A-172 cell viability was also found to be reduced synergistically with CBD and clomiphene for 48 hr of exposure in 5% serum medium (FIG. 16).

Figure 15A:
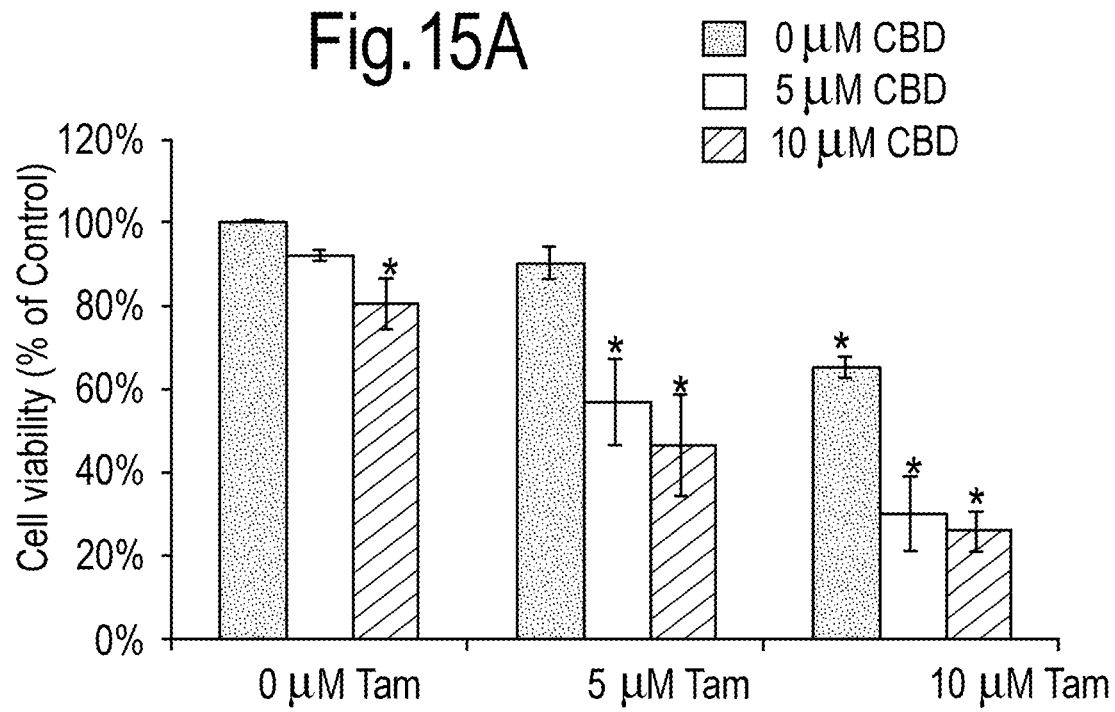
FIG. 15A graphically depicts the synergistic effect of cannabidiol with tamoxifen, on growth inhibition of MCF-7 cells incubated with different concentrations of cannabidiol, tamoxifen and vehicle in 5% FCS medium for 24h. Cell viability was determined by XTT assay.
Figure 15B:
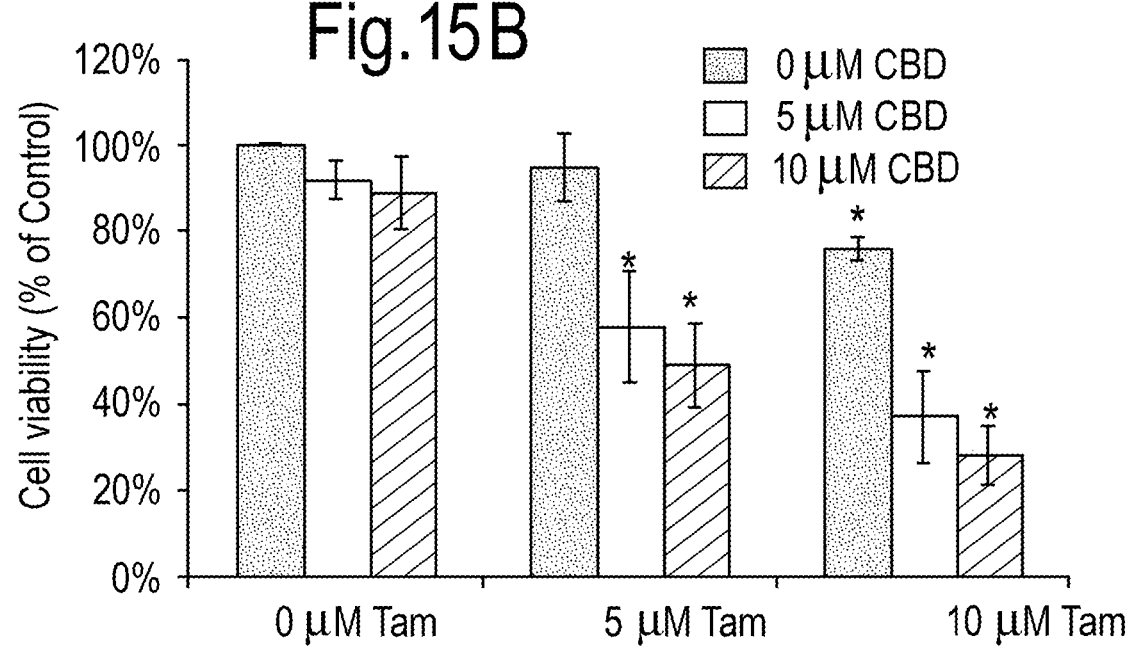
FIG. 15B graphically depicts the synergistic effect of cannabidiol with tamoxifen, on growth inhibition of MCF-7 cells pre-treated with 10 nM estradiol for 30 min, then incubated with different concentrations of cannabidiol, tamoxifen and vehicle in 5% FCS medium for 24h. Cell viability was determined by XTT assay.

To evaluate the role of ER involvement in cell viability of MCF-7 with the combination of CBD and tamoxifen, β estradiol was added 30 min before the drug treatment in order to block the ER. Interestingly there was no significant difference in cell viability between β estradiol treated and untreated groups (FIGS. 15A and 15B). Thus these results strongly showed that these drugs are acting independent of ER in reduction of cell viability.

Example 4

Nuclear Morphological Changes are Characteristics of Apoptosis

Figure 18C:
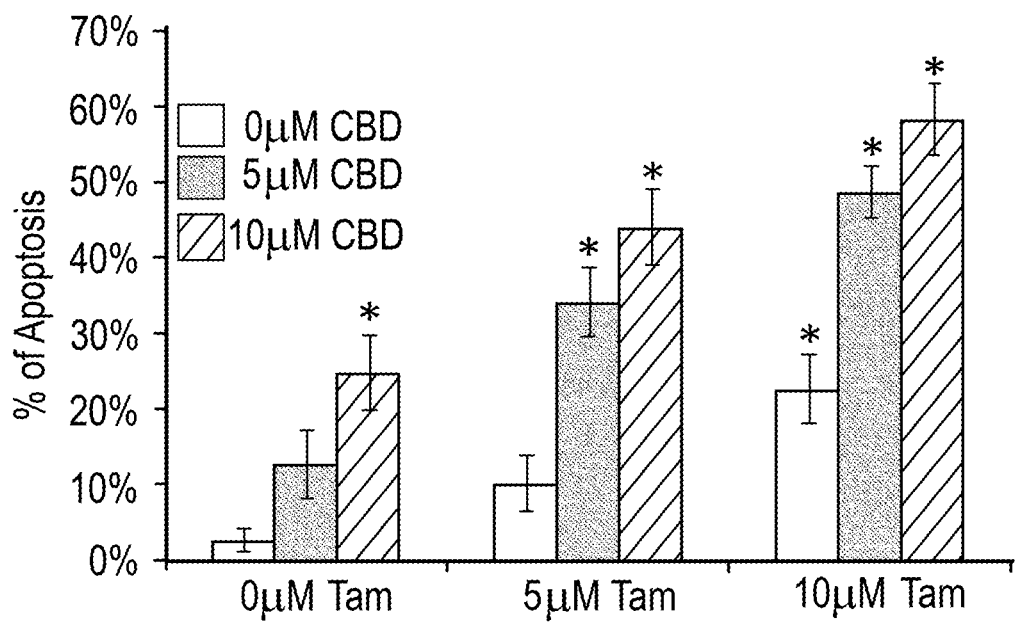
FIG. 18C graphically depicts the induction of apoptosis in CCRF-CEM cells by cannabidiol, clomiphene and tamoxifen in CCRF-CEM cells w incubated with cannabidiol, tamoxifen and vehicle in 5% FCS medium for 24h.
Figure 19:
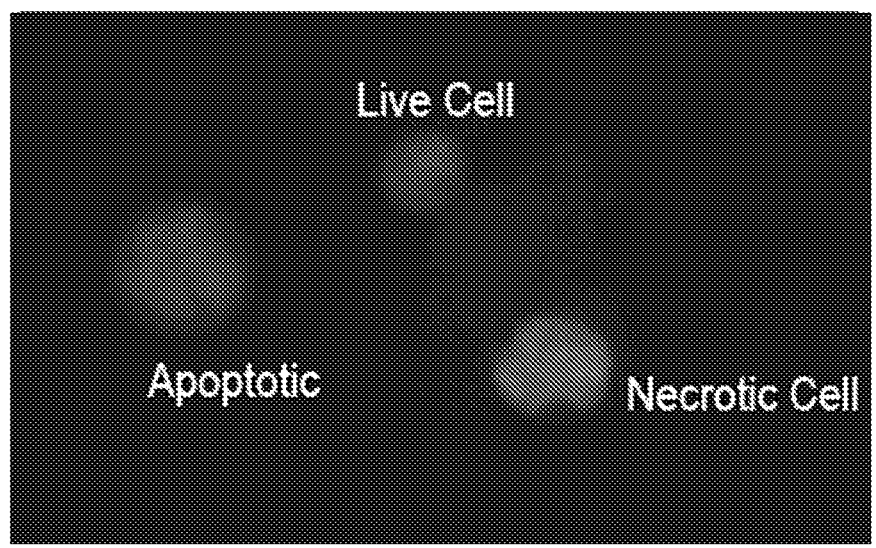
FIG. 19 is a micrograph depicting the morphological features of normal HL-60 cells and apoptotic cells were visualized by fluorescence microscopy. Original magnification X400 in cells treated with CBD for 24 h

The effect of CBD on apoptosis of cancer cell lines was examined CBD showed dose and time dependent induction of apoptosis in both HL-60 and CCRF-CEM cell lines (FIG. 17A and FIG. 18A). The combination of CBD with TPEs had a synergistic effect in induction of apoptosis whereas with menadione, CBD showed more than additive effect in induction of apoptosis of HL-60 cell line (FIGS. 17B and 17C). Similar results were also found with CCRF-CEM cell line (FIG. 18). A representative micrograph is shown in FIG. 19.

Example 5

Down-Regulation of Mcl-1 with CBD

Figure 20:
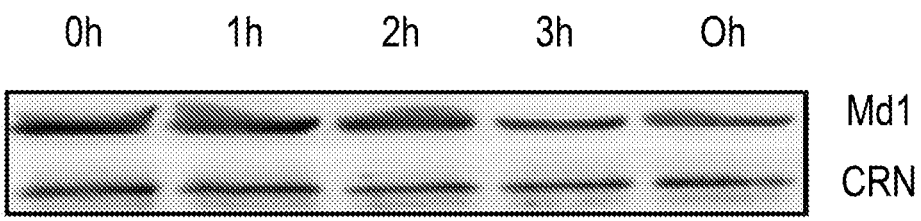
FIG. 20 depicts the effect of cannabidiol and clomiphene on down regulation of Mcl-1 in CCRF-CEM cells treated with 20 μM cannabidiol for the indicated time points. Cells were collected and washed two times with PBS, then cell lysates were prepared using RIPA buffer. Proteins were subjected to SDS-PAGE and immunoblotted with antibodies against MCl-1 and calreticulin (CRN).

Over expression of Mcl-1 is associated with survival of leukemic cells; CBD down regulated the Mcl-1 expression in CCRF-CEM cells. CBD showed the down regulation of Mcl-1 by 3h of treatment (FIG. 20).

Example 6

Figure 21A:
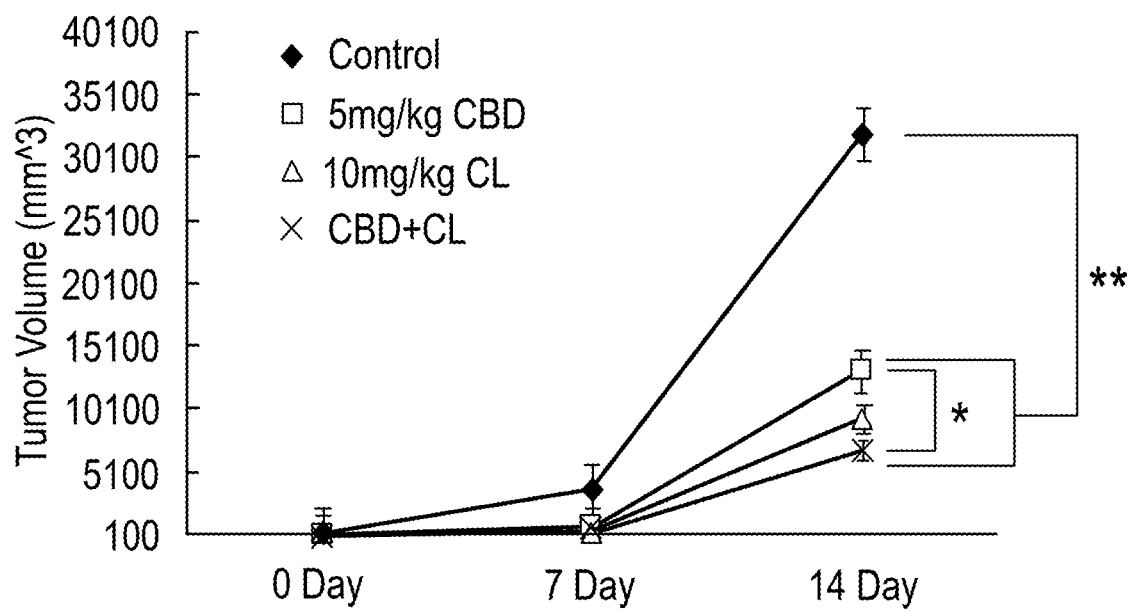
FIG. 21A graphically depicts the effect of cannabidiol, clomiphene and cannabidiol+clomiphene on tumor volume in a mouse xenograft model transplanted with HL-60 cells. Tumor volumes were measured once per week by caliper (n=6). (*: P<0.05; **: P<0.01).

Inhibition of Tumor Growth in a Mouse Xenograft Model Transplanted with HL-60 Cells Treatment of the xenografted mice with 5 mg/kg CBD, 10 mg/kg CL alone and combination resulted in significant suppression of HL-60 tumor growth from days 7 through 14 (FIG. 21).

Example 7

Effect of CBD and Clomiphene on AML and CLL Primary Cells

Figure 22A:
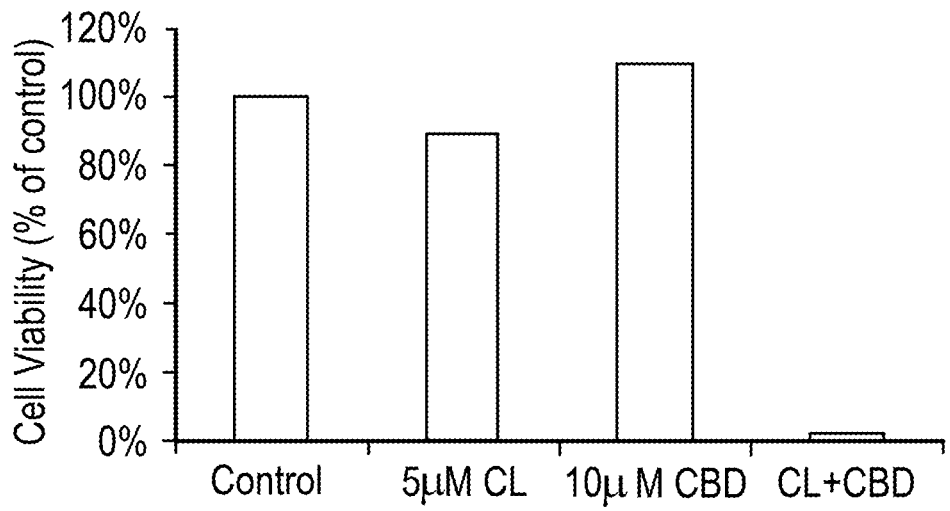
FIG. 22A graphically depicts the effect of cannabidiol and clomiphene on AML primary cells incubated with and without and clomiphene for 24h. Cell viability was measured by XTT reduction.
Figure 22B:
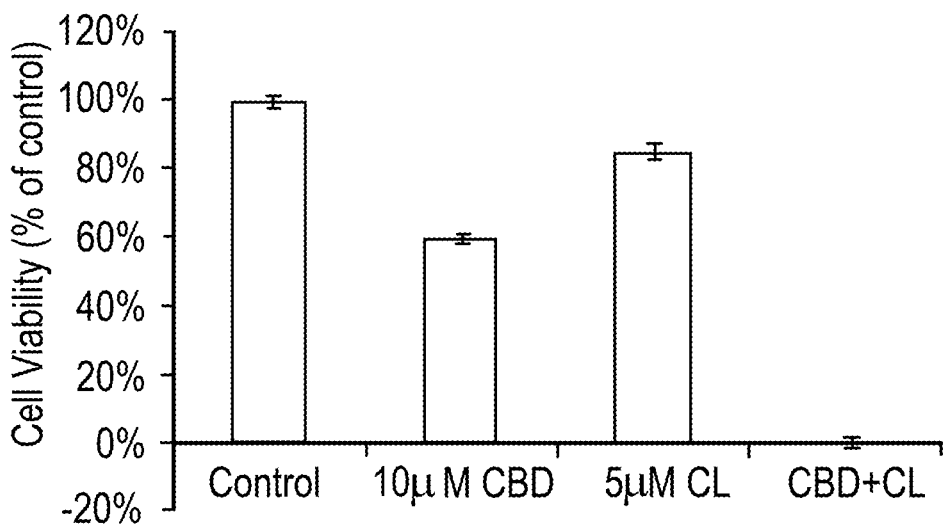
FIG. 22B graphically depicts the effect of cannabidiol and clomiphene on CLL primary cells incubated with and without and cannabidiol for 24h. Cell viability was measured by XTT reduction.

The cytotoxic effect of CBD and clomiphene on AML and CLL primary cells was evaluated, as well. 5 µM clomiphene and 10 µM CBD synergistically induced cell death within 24 hr (FIG. 22).

What is claimed is:

1. A composition comprising a synergistic combination of cannabidiol (CBD) and at least one cholesterol epoxide hydrolase/anti-estrogen binding site (ChEH/AEBS) inhibitor compound, which ChEH/AEBS inhibitor compound is not a selective estrogen receptor modulator (SERM) and is a selective inhibitor of ChEH/AEBS, wherein the CBD is present in an amount of sufficient to provide a dose of 500 mg/kg to 2000 mg/kg to a subject and the ChEH/AEBS inhibitor compound is present in an amount sufficient to provide a dose of 500 mg/kg to 2000 mg/kg to the subject, and the selective inhibitor is 1-[2-[4-(phenylmethyl)phenoxy[ethy[-Pyrrolidine (PBPE) or tesmilifene (DPPE).

2. The composition of claim 1, wherein the selective inhibitor is DPPE.

3. The composition of claim 1, further comprising a pharmaceutically acceptable carrier.

4. An anti-cancer pharmaceutical composition which comprises the composition of claim 3 in a therapeutically effective amount.

5. A method of treating leukemia, breast cancer, or glioblastoma, said method comprising administering to a subject in need thereof a therapeutically effective amount of the composition of claim 3.

6. A method for treating a subject in need of leukemia, breast cancer, or glioblastoma therapy, which comprises administering to the subject a therapeutically effective amount of the composition of claim 1 for the treatment of leukemia, breast cancer, or glioblastoma.

7. The method of claim 6, wherein the selective inhibitor is DPPE.

8. The method of claim 5, wherein the composition is administered intravenously, orally, or sublingually.

9. The method of claim 5, wherein the composition is administered to the subject for a duration of between 24 hours to 14 days, or between 24 hours to 30 days.

10. The method of claim 5, wherein administration of the composition suppresses tumor growth.

11. The method of claim 10, wherein suppression of tumor growth comprises a reduction in tumor size or maintaining the tumor size.

12. The method of claim 10, further comprising comparing the tumor growth to a pre-treatment tumor size, volume, or both.

13. The method of claim 6, wherein the composition is administered intravenously, orally, or sublingually, or a combination thereof.

14. The method of claim 6, wherein the composition is administered to the subject for a duration of between 24 hours to 14 days, or between 24 hours to 30 days.

15. The method of claim 6, wherein administration of the composition suppresses tumor growth.

16. The method of claim 15, wherein suppression of tumor growth comprises a reduction in tumor size or maintaining the tumor size.

17. The method of claim 15, further comprising comparing the tumor growth to a pre-treatment tumor size, volume, or both.

* * * * *